United States Patent [19]

Mousa

[11] Patent Number: 6,056,958
[45] Date of Patent: *May 2, 2000

[54] METHOD OF TREATMENT OF ARTERIAL AND VENOUS THROMBOEMBOLIC DISORDERS

[75] Inventor: Shaker Ahmed Mousa, Lincoln University, Pa.

[73] Assignee: Dupont Pharmaceuticals, Wilmington, Del.

[ * ] Notice: This patent issued on a continued prosecution application filed under 37 CFR 1.53(d), and is subject to the twenty year patent term provisions of 35 U.S.C. 154(a)(2).

[21] Appl. No.: 08/901,344

[22] Filed: Jul. 28, 1997

Related U.S. Application Data

[63] Continuation of application No. 08/353,419, Dec. 9, 1994, abandoned.

[51] Int. Cl.$^7$ .................................................. A61K 39/395
[52] U.S. Cl. ..................... 424/145.1; 424/141.1; 424/130.1; 514/2
[58] Field of Search ............................... 360/32, 64, 33.1, 360/72.2; 514/2; 386/27, 33, 37, 40–41, 109, 123; 424/145.1, 141.1, 130.1

[56] References Cited

FOREIGN PATENT DOCUMENTS

| | | |
|---|---|---|
| 0578083 | 1/1994 | European Pat. Off. . |
| 02289598 | 4/1989 | Japan . |
| WO8905155 | 6/1989 | WIPO . |
| WO9200995 | 1/1992 | WIPO . |
| WO9320229 | 10/1993 | WIPO . |
| WO9415958 | 7/1994 | WIPO . |

OTHER PUBLICATIONS

Charo et al, Journal of Biological Chemistry, vol. 262 (21), Jul. 25, 1987, pp. 9935–9938.

Yue, Tian–Li; McKenna, Patrick J.; Ohlstein, Eliot H.; Farach–Carson, Mary C.; Butler, William T.; Johanson, Kyung; McDevitt, Patrick; Feuerstein, Giora Z.; and Stadel, Jeffrey M., Exp. Cell Res. 1994, 214, 459, "Osteopontin–Stimulated Vascular Smooth Muscle Cell Migration Is Mediated by $\beta_3$ Integrin".

Shaker A. Mousa et al., Circulation, 1994, 89 (1), 3, "Antiplatelet and Antithrombotic Efficacy of DMP 728, a Novel Platelet GPIIb/IIIa Receptor Antagonist".

Rote, William E.; Mu, Dun Xue; Bates, Eric R.; Nedelman, Mark A.; and Luchesi, Benedict R., Journal of Cardiovascular Pharmacology, 1994, 23:194–202, "Prevention of Rethrombosis After Coronary Thrombolysis in a Chronic Canine Model. I. Adjunctive Therapy with Monoclonal Antibody 7E3 F(ab')$_2$ Fragment".

*Primary Examiner*—Keith B. MacMillan
*Assistant Examiner*—T. D. Wessendorf
*Attorney, Agent, or Firm*—David H. Vance; Kenneth B. Rubin

[57] ABSTRACT

This invention relates to a method of prevention and/or treatment of thrombosis in a mammal without significantly altering bleeding time or coagulation. This invention further relates to methods of using selective inhibitors of the binding of vitronectin to the $\alpha_v\beta_3$ receptor, alone or in combination with other therapeutic agents, for the inhibition of thrombus formation and/or the treatment of thromboembolic disorders.

12 Claims, No Drawings

SEQUENCE LISTING (1) GENERAL INFORMATION:

(iii) NUMBER OF SEQUENCES:6

(2) INFORMATION FOR SEQ ID NO:1:

(i) SEQUENCE CHARACTERISTICS:
      (A) LENGTH:4 amino acids
      (B) TYPE:amino acid
      (C) TOPOLOGY:circular (ii) MOLECULE TYPE:peptide (vi) ORIGINAL SOURCE:synthetic (ix) FEATURE:
            (D) OTHER INFORMATION: Note:  Positions 1 and 4 are joined by
                -C(O)-(CH2)n-R3-(CHR1)n-NR2.
            (D) OTHER INFORMATION: Note:  Position 1 is selected from Ala,
                Val, Ile, Leu, Nle, phenylGly, Phe, Lys, Orn, Met, Pro,
                b-Ala, Tyr, Ser, NMeGly, cyclohexylGly,
                cyclohexylmethylGly, norvaline, 2_aminobutyric acid,
                2_aminopentanoic acid, Gly, Cys, S-benzyl-Cys,
                S_methyl-Cys, Asp, Glu, 2-amino-2-methylpropionic acid,
                His, 1-allo-isoleucine, Asn, Gln, Thr, Trp, or
                O-methyl-Tyr. (D) OTHER INFORMATION:Note:  Position 2 is
                selected from Arg, Nd-Me-Nd-guanidinylOrn, Lys,
                p-aminomethylPhe, p-guanidinylPhe, or Ne_MeLys.
            (D) OTHER INFORMATION:Note:  Position 4 is selected from
                Asp, b-MeAsp, NMeAsp, Asp_(methylcarbonyloxymethyl ester)
                ,Asp-(ethylcarbonyloxymethyl ester),
                Asp_(t-butylcarbonyloxymethyl ester),
                Asp_(cyclohexylcarbonyloxymethyl ester),
                Asp_(1-(methylcarbonyloxy)ethyl ester),
                Asp_(1-(ethylcarbonyloxy)ethyl ester),
                Asp_(1-(t-butylcarbonyloxy)ethyl ester),
                Asp_(1-(cyclohexylcarbonyloxy)ethyl ester),
                Asp_(i-propyloxycarbonyloxymethyl ester),
                Asp_(cyclohexyloxycarbonyloxymethyl ester),
                Asp_(t-butyloxycarbonyloxymethyl ester),
                Asp_(1-(i-propyloxycarbonyloxy)ethyl ester),
                Asp_(1-(cyclohexyloxycarbonyloxy)ethyl ester),
                Asp_(1-(t-butyloxycarbonyloxy)ethyl ester),
                Asp_(dimethylaminoethyl ester),
                Asp_(diethylaminoethyl ester),
                Asp_((1,3-dioxa-5-methyl-cyclopenten-2-one-4-yl)methyl
                ester), Asp_((5-(t-butyl)-1,3-dioxa-cyclopenten-2
                -one-4-yl)methyl ester),
                Asp_((1,3-dioxa-5-phenyl-cyclopenten-2-one-4-yl)
                methyl ester), or
                Asp_(1-(2-(2-methoxypropyl)carbonyloxy)ethyl ester).

(xi) SEQUENCE DESCRIPTION:SEQ ID NO:1:

Xaa Xaa Gly Xaa
1

(2) INFORMATION FOR SEQ ID NO:2:

(i) SEQUENCE CHARACTERISTICS:
        (A) LENGTH:4 amino acids
        (B) TYPE:amino acid
        (C) TOPOLOGY:circular (ii) MOLECULE TYPE:peptide (vi) ORIGINAL SOURCE:synthetic (ix) FEATURE:
        (D) OTHER INFORMATION:  Note:  Positions 1 and 4 are
            joined through a meta-aminomethylbenzoic acid.

(xi) SEQUENCE DESCRIPTION:SEQ ID NO:2:

Ala Arg Gly Asp
1

(2) INFORMATION FOR SEQ ID NO:3:

(i) SEQUENCE CHARACTERISTICS:
        (A) LENGTH:4 amino acids
        (B) TYPE:amino acid
        (C) TOPOLOGY:circular (ii) MOLECULE TYPE:peptide (vi) ORIGINAL SOURCE:synthetic -continued

```
    (ix) FEATURE:
        (D) OTHER INFORMATION:  Note:  Positions 1 and 4 are joined
            through a meta-aminomethylbenzoic acid.

(xi) SEQUENCE DESCRIPTION:SEQ ID NO:3:

Pro Arg Gly Asp
1

(2) INFORMATION FOR SEQ ID NO:4:

(i) SEQUENCE CHARACTERISTICS:
        (A) LENGTH:4 amino acids
        (B) TYPE:amino acid
        (C) TOPOLOGY:circular (ii) MOLECULE TYPE:peptide (vi) ORIGINAL SOURCE:synthetic (ix) FEATURE:
        (D) OTHER INFORMATION:  Note:  Positions 1 and 4 are joined
            through a meta-aminomethylbenzoic acid.

(xi) SEQUENCE DESCRIPTION:SEQ ID NO:4:

Ser Arg Gly Asp
1

(2) INFORMATION FOR SEQ ID NO:5:

(i) SEQUENCE CHARACTERISTICS:
        (A) LENGTH:4 amino acids
        (B) TYPE:amino acid
        (C) TOPOLOGY:circular (ii) MOLECULE TYPE:peptide (vi) ORIGINAL SOURCE:synthetic (ix) FEATURE:
        (D) OTHER INFORMATION:  Note:  Positions 1 and 4 are joined
            through a meta-aminomethylbenzoic acid.

(xi) SEQUENCE DESCRIPTION:SEQ ID NO:5:

Leu Arg Gly Asp
1

(2) INFORMATION FOR SEQ ID NO:6:

(i) SEQUENCE CHARACTERISTICS:
        (A) LENGTH:4 amino acids
        (B) TYPE:amino acid
        (C) TOPOLOGY:circular (ii) MOLECULE TYPE:peptide (vi) ORIGINAL SOURCE:synthetic (ix) FEATURE:
        (D) OTHER INFORMATION:  Note:  Positions 1 and 4 are joined
            through a meta-aminomethylbenzoic acid.

(xi) SEQUENCE DESCRIPTION:SEQ ID NO:6:

Lys Arg Gly Asp
```

METHOD OF TREATMENT OF ARTERIAL AND VENOUS THROMBOEMBOLIC DISORDERS

This is a continuation of application Ser. No. 08/353,419 filed Dec. 9, 1994, now abandoned.

FIELD OF THE INVENTION

This invention relates to a method of prevention and/or treatment of thrombosis in a mammal without significantly altering bleeding time or coagulation. This invention further relates to methods of using selective inhibitors of the binding of vitronectin to the $\alpha_v\beta_3$ receptor, alone or in combination with other therapeutic agents, for the inhibition of thrombus formation and/or the treatment of thromboembolic disorders.

BACKGROUND OF THE INVENTION

Intravascular thrombosis is one of the most frequent pathological events accounting for greater than 50% of all deaths as well as a variety of other serious clinical problems. Factors which stimulate thrombosis include vascular damage, activation/stimulation of platelets, and activation of the coagulation cascade. Platelet activation and subsequent aggregation leads to the exposure of phospholipid on the platelet surface which facilitates the activation of coagulation factors X and II. Platelet activation and the resulting aggregation has been shown to be associated with various pathological conditions including cardiovascular and cerebrovascular thromboembolic disorders such as unstable angina, myocardial infarction, transient ischemic attack, and stroke.

When a blood vessel is injured, either acutely or chronically, for example, by clinical interventions or pathophysiological processes, such as atherosclerosis, platelets and leukocytes may be activated and may adhere to the injured blood vessel surface, as well as to each other in a homotypic and heterotypic fashion. Such activation, primary adhesion, and secondary homotypic and heterotypic cellular aggregation, involving cell-associated and soluble adhesion proteins (also referred to as adhesive proteins), including fibrinogen, leads to occlusive thrombus formation in the lumen of the blood vessel. The family of receptor proteins which recognize and bind adhesion proteins are referred to as integrins.

During endothelium injury, the basement membrane zones of blood vessels express several adhesion proteins, including von Willebrand factor, fibronectin, and fibrin. Additionally, several members of the integrin family of adhesion protein receptors are expressed on the surface of endothelial, smooth muscle and on other circulating cells.

Among these integrins is $\alpha_v\beta_3$, the endothelial cell, fibroblast, and smooth muscle cell receptor for adhesion proteins including von Willebrand factor, fibrinogen (fibrin), vitronectin, thrombospondin, and osteopontin.

It has been reported that the integrin $\alpha_v\beta_3$ is expressed on blood vessels in granulation tissue and that enhanced expression of $\alpha_v\beta_3$ in human blood vessels occurs during angiogenesis (Brooks et al. Science 1994, 264: 569–571). Anti-$\alpha_v\beta_3$ antibody was reported to block bFGF-induced angiogenesis, suggesting a potential role of $\alpha_v\beta_3$ in angiogenesis. Additionally, $\alpha_v\beta_3$ has been implicated in tumor progression and neovascularlization (Brooks et al. Science 1994, 264 5158: 569–571).

Monoclonal antibody, LM609 (produced by hybridoma LM609 ATCC HB 9537), disclosed in PCT Application Publication No. WO 89/05155 (published Jun. 15, 1989) and Cheresh et al., J. Biol. Chem. 1987, 262:17703–17711 binds to $\alpha_v\beta_3$ complex. PCT Application Publication No. WO 93/20229 discloses monoclonal antibodies, which bind to the $\alpha_v\beta_3$ receptor expressed on the surface of osteoclasts. Monoclonal antibody 23C6, which binds to $\alpha_v\beta_3$ was reported to be able to disrupt osteoclast function (Horton et al., Cancer Res., 1985, 45:5663–5669; Horton et al., Exp. Cell. Res., 1991, 195:368–375). Monoclonal antibody 13C2 (Horton et al., Cancer Res., 1985, 45:5663-5669) was shown to bind the $\alpha_v$ portion of the $\alpha_v\beta_3$ molecule, whereas several other monoclonal antibodies were reported to recognize the $\beta_3$ portion (Nesbitt et al., in "Leukocyte Typing IV, White Cell Differentiation Antigens", Knapp et al. (eds.) 1991, p. 1037). The specific monoclonal antibodies variously reported in the art were shown to also bind to endothelial cells and various melanoma cell lines.

It is well known that platelet activation and aggregation are implicated in various thromboembolic disorders. Platelet aggregation is known to involve the binding of fibrinogen to the activated membrane surface integrin, the fibrinogen receptor GPIIb/IIIa. Inhibition of platelet aggregation by inhibition of GPIIb/IIIa to fibrinogen is, therefore, recognized as an attractive target for antithrombotic therapeutic intervention. A variety of GPIIb/IIIa antagonists are presently in clinical development for the treatment of thrombosis.

Similarly, inhibitors of thrombin have been demonstrated to have antithrombotic efficacy in various arterial and venous thrombosis models.

However, it is recognized that the inhibition of platelet aggregation or thrombin may result in a hemostatic imbalance with consequent bleeding time prolongation and in clinical situations bleeding complications and bleeding risk may arise (Simoons et al., Circulation 1994, 89:596–603; Cannegieter et al., Circulation 1994, 89: 635–641; FDC Reports: Pink Sheet, Vol. 56, 1994). Increased bleeding risk has been associated with both GPIIb/IIIa antagonist and thrombin inhibitor antithrombotic therapies (The Guesto IIa Investigators, U.S., Canada, Europe, Australia and New Zealand, Circulation 1994, 40 (I-231): 1240; Lefkovits et al., Circulation 1994, 40 (I-231): 3037; Tcheng et al., Circulation 1994, 90: 1757–1764; Antman et al., Circulation 1994; 90: 1624–1630). Furthermore in the case of direct or indirect thrombin inhibitors, a rebound activation of the coagulation system has been demonstrated upon the discontinuation of these therapies (Theroux al., N. Engl. J. Med. 1992, 327:141–145; Gold et al., J. Am. Coll. Cardiol. 1993, 21:1039–1047).

In view of the inherent limitations of the presently available GPIIb/IIIa antagonist and thrombin inhibitor approaches for antithrombotic therapy, there is a need for new therapeutic targets for the treatment and prevention of thrombosis which are more effective and safer than present antithrombotic therapeutic approaches. An ideal antithrombotic strategy would prevent arterial and venous thrombotic disorders, without significantly affecting the hemostatic balance, that is, without significantly affecting platelet aggregation functions or the blood coagulation parameters. The present invention provides new methods for the treatment (including prevention) of thrombosis which do not significantly alter hemostatic balance and do not significantly inhibit platelet aggregation and do not significantly inhibit coagulation. A preferred aspect of the present invention comprises methods of treatment (including prevention) of thrombosis and/or thromboembolic disorders comprising administering to a subject in need of such treatment an agent that selectively inhibits the binding of vitronectin to the $\alpha_v\beta_3$ receptor.

None of the above references teach or suggest the use of an $\alpha_v\beta_3$ receptor selective ligand to prevent thrombus formation.

SUMMARY OF THE INVENTION

The present invention provides methods for the prevention of arterial or venous thrombosis and/or treatment of thromboembolic disorders in a mammal without significantly inhibiting platelet aggregation or blood coagulation. A preferred aspect of the present invention comprises methods of treatment, including prevention, of thrombosis and/or thromboembolic disorders comprising administering to a subject in need of such treatment an agent, including a protein, peptide, or a nonpeptide compound, said agent being substantially more effective as an inhibitor of the binding of vitronectin to $\alpha_v/\beta_3$ than as an inhibitor of the binding of fibrinogen to GPIIb/IIIa. Preferred agents useful in the method of the present invention exhibit high affinity inhibition of the binding of vitronectin to $\alpha_v/\beta_3$ and exhibit low affinity inhibition of the binding of fibrinogen to GPIIb/IIIa.

Another preferred aspect of the present invention comprises methods of treatment, including prevention, of thrombosis and/or thromboembolic disorders comprising administering to a subject in need of such treatment an agent, said agent being substantially more effective as an inhibitor of the binding of vitronectin to $\alpha_v/\beta_3$ than as an inhibitor of platelet aggregation.

Preferred agents useful in the method of the present invention display selectivity as ligands for $\alpha_v/\beta_3$ relative to GPIIb/IIIa, such that antithrombotic effects are observed in vivo following administration of the agent without causing significant antiplatelet effects or increased bleeding time.

Other agents useful for the method of the present invention may also display affinity for other non-GPIIb/IIIa integrins or other adhesion protein receptors present in the extracellular matrix.

Compounds useful in the method of the present invention for the treatment of thrombosis include monoclonal antibodies that immunoreact with $\alpha_v/\beta_3$ and block the binding of vitronectin to $\alpha_v/\beta_3$. Compounds useful in the method of the present invention also include certain cyclic RGD-containing compounds.

The present invention also includes methods of using such selective $\alpha_v/\beta_3$ ligands in combination with one or more additional agent(s) for the treatment and/or prevention of thromboembolic disorders, said additional agent being selected from: anti-coagulants such as warfarin or heparin; anti-platelet agents such as GPIIb/IIIa inhibitors, aspirin, piroxicam or ticlopidine; thrombin inhibitors such as boropeptides, hirudin or argatroban; or thrombolytic agents such as tissue plasminogen activator, anistreplase, urokinase or streptokinase.

DETAILED DESCRIPTION OF THE INVENTION

The present invention provides methods for the prevention of arterial or venous thrombosis and/or treatment of thromboembolic disorders in a mammal without significantly inhibiting platelet aggregation or blood coagulation. A preferred aspect of the present invention comprises methods of treatment, including prevention, of thrombosis and/or thromboembolic disorders comprising administering to a subject in need of such treatment an agent, including a protein, peptide, or a nonpeptide compound, said agent being substantially more effective as an inhibitor of the binding of vitronectin to $\alpha_v/\beta_3$ than as an inhibitor of the binding of fibrinogen to GPIIb/IIIa. Preferred agents useful in the method of the present invention exhibit high affinity inhibition of the binding of vitronectin to $\alpha_v/\beta_3$ and exhibit low affinity inhibition of the binding of fibrinogen to GPIIb/IIIa.

Another preferred aspect of the present invention comprises methods of treatment, including prevention, of thrombosis and/or thromboembolic disorders comprising administering to a subject in need of such treatment an agent, said agent being substantially more effective as an inhibitor of the binding of vitronectin to $\alpha_v/\beta_3$ than as an inhibitor of platelet aggregation.

Preferred agents useful in the method of the present invention display selectivity as ligands for $\alpha_v/\beta_3$ relative to GPIIb/IIIa, such that antithrombotic effects are observed in vivo following administration of the agent without causing significant antiplatelet effects or increased bleeding effects.

Other agents useful for the method of the present invention may also display affinity or be selective for other non-GPIIb/IIIa integrins or other adhesion protein receptors present in the extracellular matrix.

Compounds useful in the method of the present invention for the treatment of thrombosis include monoclonal antibodies that immunoreact with $\alpha_v/\beta_3$ and block the binding of vitronectin to $\alpha_v/\beta_3$. Compounds useful in the method of the present invention also include certain cyclic RGD-containing compounds.

In the present invention, it has been discovered that compounds which display selectivity as ligands for the vitronectin receptor $\alpha_v/\beta_3$ relative to the GPIIb/IIIa receptor have unexpected utility for the treatment and prevention of thrombus formation.

The present invention comprises methods of treatment, including prevention, of thrombosis and/or thromboembolic disorders comprising administering to a subject in need of such treatment an $\alpha_v/\beta_3$ selective ligand. The term "$\alpha_v/\beta_3$ selective ligand" or "$\alpha_v/\beta_3$ ligand" as used herein means any agent or compound, including protein, peptide, and nonpeptide compounds, that is substantially more effective as an inhibitor of the binding of vitronectin to $\alpha_v/\beta_3$ than as an inhibitor of the binding of fibrinogen to GPIIb/IIIa. Preferred $\alpha_v/\beta_3$ ligands are those exhibiting high affinity inhibition of the binding of vitronectin to $\alpha_v/\beta_3$ and low affinity inhibition of the binding of fibrinogen to GPIIb/IIIa. Also preferred in the present invention are $\alpha_v/\beta_3$ ligands having selectivity or significantly higher affinity for the $\alpha_v/\beta_3$ receptor relative to other cellular proteins, in particular, other adhesion protein receptors or integrins.

Preferred $\alpha_v/\beta_3$ ligand compounds useful in the method of the present invention are those having substantially higher affinity for $\alpha_v/\beta_3$ relative to GPIIb/IIIa.

Preferred $\alpha_v/\beta_3$ selective ligands useful in the present invention comprise agents which are substantially more effective as inhibitors of the binding of vitronectin to $\alpha_v/\beta_3$ than as inhibitors of platelet aggregation. Such $\alpha_v/\beta_3$ ligands, when administered to a subject at a therapeutically effective dose for the treatment (including prevention) of arterial and/or venous thromboembolic disorders, cause relatively little or no significant increased bleeding effects or antiplatelet effects in vivo in the subject. Thus, the $\alpha_v/\beta_3$ selective ligands of the present invention result in substantially reduced undesired effects on bleeding time and blood coagulation than other known therapeutic agents for the treatment of thrombosis, such as GPIIb/IIIa antagonists, which have substantially greater affinity for GPIIb/IIIa than for $\alpha_v/\beta_3$.

Compounds useful in the method of the present invention are those that selectively inhibit the binding of vitronectin to $\alpha_v/\beta_3$ or that inhibit the binding to $\alpha_v/\beta_3$ of other adhesion or adhesive proteins which bind competitively with vitronectin to $\alpha_v/\beta_3$ and/or that bind to $\alpha_v/\beta_3$ via the Arg-Gly-Asp (RGD) sequence, including von Willebrand factor, fibrinogen, thrombospondin, and osteopontin.

It has been discovered in the present invention that the blockade of the vitronectin receptor $\alpha_v/\beta_3$ results in increased vessel wall passivity resulting in a significant reduction of arterial and venous thrombotic events without any significant apparent effects on the hemostatic system, that is, without causing significant effects on bleeding times or the coagulation parameters.

The vitronectin receptor $\alpha_v/\beta_3$ is a heterodimer membrane-associated protein which has been described in platelets, leukocytes, endothelial cells, fibroblasts, and smooth muscle cells. The $\alpha_v/\beta_3$ receptor consists of an $\alpha$-subunit ($\alpha_v$) of 135 kDa having an amino acid sequence which is 35% identical with the GPIIb subunit of GPIIb/IIIa. The $\alpha_v/\beta_3$ receptor $\beta$-subunit ($\beta_3$) of 110 kDa is identical in amino acid sequence to the GPIIIa subunit of GPIIb/IIIa. Like GPIIb/IIIa, the vitronectin receptor $\alpha_v/\beta_3$ binds several RGD-containing adhesive proteins such as vitronectin, fibronectin, von Willebrand factor, fibrinogen, and thrombosponden, said binding requiring the RGD sequence. The RGD-binding domain of $\alpha_v/\beta_3$ has been shown to include amino acids within residues 139–349 of the vitronectin receptor $\alpha$-subunit, and residues 61–203 of the $\beta$-subunit.

The present invention provides a novel and unexpected method for preventing both arterial and venous thrombosis which does not involve inhibition of either platelet GPIIb/IIIa or thrombin. The present invention also provides a novel method for preventing both arterial and venous thrombosis, which comprises administering a selective $\alpha_v/\beta_3$ ligand lacking or having relatively low affinity for GPIIb/IIIa relative to that exhibited for $\alpha_v/\beta_3$. This novel strategy provides a method of treating thrombosis or thromboembolic disorders without causing significant effects on platelet aggregation or the coagulation cascade or increasing bleeding time.

The method of the present invention is useful for the prevention of abrupt closure and restenosis which occurs at variable time frames post-angioplasty or post-thrombolysis. Thus, selective $\alpha_v/\beta_3$ ligands may be used in accordance with the present invention as an adjunct to thrombolytic therapy and angioplasty to prevent reocclusion. The method of using selective $\alpha_v/\beta_3$ ligands in accordance with the present invention is also useful for prophylaxis of cerebrovascular disorders, such as, cerebral thrombosis or embolism in stroke or transient ischemic attacks, and ischemic heart diseases, for example and without limitation, myocardial infarction or peripheral circulatory disorders.

In accordance with the present invention, selective $\alpha_v/\beta_3$ ligands may be used for the treatment (including prevention) of conditions involving thrombus or embolus formation, such as arterial or venous cardiovascular or cerebrovascular thromboembolic disorders, including, for example, thromboembolic disorders associated with unstable angina, recurrent myocardial infarction, ischemic sudden death, transient ischemic attack, stroke, atherosclerosis, deep vein thrombosis, or pulmonary embolism, by administering to a host in need of such treatment a pharmaceutically effective amount of such $\alpha_v/\beta_3$ ligand compound.

The term "thromboembolic disorders" as used herein includes conditions involving arterial or venous cardiovascular or cerebrovascular thromboembolic disorders, including, for example, conditions involving platelet activation and aggregation, thrombosis, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, myocardial infarction, cerebral embolism, kidney embolisms, pulmonary embolisms, or such disorders associated with diabetes.

The $\alpha_v/\beta_3$ ligand compounds suitable for use in the method of the present invention include proteins such as antibodies and fragments of antibodies, peptides, cyclic peptides, peptidomimetic compounds, or non-peptide compounds that selectively bind to the $\alpha_v/\beta_3$ receptor and block the binding of vitronectin, or ligands which bind competitively with vitronectin, to the $\alpha_v/\beta_3$ receptor. Such compounds preferably bind to the RGD-binding domain of the $\alpha_v/\beta_3$ receptor. Examples of such $\alpha_v/\beta_3$ ligand compounds include compounds which mimic the RGD sequence and bind specifically to the RGD binding domain of the $\alpha_v/\beta_3$ receptor. Examples of such compounds include cyclic RGD-containing compounds or RGD peptidomimetic compounds. In addition, such compounds preferably bind to the $\alpha_v/\beta_3$ receptors expressed on endothelial cell, smooth muscle cell, and/or fibroblasts. As discussed above, the $\alpha_v/\beta_3$ ligand compounds useful in the present invention lack or have low affinity for GPIIb/IIIa relative to that exhibited for $\alpha_v/\beta_3$ and do not significantly block or only relatively weakly block the binding of fibrinogen to GPIIb/IIIa.

Compounds useful in the method of the present invention may also display affinity or selectivity as ligands for other non-GPIIb/IIIa integrins or adhesion protein receptors in the extracellular matrix and may act to inhibit the binding of other adhesion proteins to such other non-GPIIb/IIIa integrins or adhesion protein receptors.

Preferred $\alpha_v/\beta_3$ ligands useful in the method of the present invention with high affinity for the $\alpha_v/\beta_3$ receptor are effective in preventing thrombosis formation, without significantly affecting bleeding time or coagulation, thereby providing an improved therapeutic approach for the treatment of acute and chronic thromboembolic disorders. Moreover, as noted above, the present therapeutic method may be an effective adjunctive therapy and be complementary with other methods of therapy for the treatment of thromboembolic disorders.

Preferred $\alpha_v/\beta_3$ ligands useful in the method of the present invention are those having an $IC_{50}$ for the inhibition of the binding of vitronectin to the $\alpha_v/\beta_3$ receptor of less than about 10 nM and an an $IC_{50}$ for for the inhibition of fibrinogen binding to GPIIb/IIIa of greater than about 300 nM. Such $IC_{50}$ values may be determined in an in vitro binding assay, such as the in-vitro binding assays using purified $\alpha_v/\beta_3$ and GPIIb/IIIa as described herein below. More preferred $\alpha_v/\beta_3$ ligands useful in the method of the present invention are those having an $IC_{50}$ for the inhibition of vitronectin binding to $\alpha_v/\beta_3$ receptor of less than about 5 nM and an $IC_{50}$ for the inhibition of fibrinogen binding to GPIIb/IIIa of greater than about 1000 nM, as measured in an in vitro binding assay.

Preferred compounds useful in the method of the present invention are those compounds that have an $IC_{50}$ for the inhibition of the binding of vitronectin to the $\alpha_v/\beta_3$ receptor of less than about 10 nM, as measured in an in-vitro binding assay, such as the assay described herein below, and an $IC_{50}$ for the inhibition of platelet aggregation of greater than about 1 $\mu$M, as measured in an in vitro platelet aggregation assay, such as the assay described herein below. Further preferred compounds useful in the method of the present invention are those compounds that have an $IC_{50}$ Of less than about 5 nM in the $\alpha_v/\beta_3$-vitronectin binding assay and an $IC_{50}$ in the platelet aggregation assay described below of greater than about 10 µM.

The inhibition of binding of vitronectin, or the inhibition of the binding of a ligand that binds competitively with vitronectin, to $\alpha_v/\beta_3$ in accordance with the present invention can be determined by standard competitive binding methods that are well known to one of skill in the art. The inhibition parameter for the inhibition of the binding of vitronectin to $\alpha_v/\beta_3$, such as an $IC_{50}$ or Ki value, is preferably measured in a cell-free or cellular in vitro system, such as in the $\alpha_v/\beta_3$ binding assay described below. As is known in the art, binding assays include competitive binding assays, such as those which rely on the ability of a test compound to compete for binding to $\alpha_v/\beta_3$ with a standard compound.

Similarly, as described above for $\alpha_v/\beta_3$, inhibition parameters for the inhibition of binding of fibrinogen, or the inhibition of the binding of a ligand that binds competitively with fibrinogen, to GPIIb/IIIa may be determined.

Inhibition parameters, such as $IC_{50}$ or Ki values, for a test agent for the inhibition of platelet aggregation can be determined using methods well known to one of skill in the art. Preferably the inhibition parameter of platelet aggregation is determined in an in vitro assay such as the assay described herein below.

The relative effectiveness of a test agent as an inhibitor of vitronectin binding to $\alpha_v/\beta_3$ as compared with the effectiveness of the test agent as an inhibitor of fibrinogen to GPIIb/IIIa can be determined by comparing the inhibition parameters for each system as described above. Thus, the $IC_{50}$ or Ki values in the above-described binding assays may be compared to determine the relative effectiveness. Similarly, inhibition parameters can be compared to measure the relative effectiveness of the test agent as an inhibitor of vitronectin binding to $\alpha_v/\beta_3$ as compared with the effectiveness of the test agent as an inhibitor of platelet aggregation.

Suitable $\alpha_v/\beta_3$ ligands useful in the method of the present invention include $\alpha_v/\beta_3$-specific monoclonal antibodies and fragments thereof which block the binding of vitronectin to $\alpha_v/\beta_3$. Thus, the present invention provides methods of prevention of arterial or venous thrombosis and/or treatment of thromboembolic disorders which comprise administering a vitronectin-blocking monoclonal antibody specific for $\alpha_v/\beta_3$. Preferred monoclonal antibodies useful in the present invention are anti-$\alpha_v/\beta_3$ monoclonal antibodies capable of inhibiting the binding of $\alpha_v/\beta_3$ expressing cells to vitronectin.

Preferred monoclonal antibodies useful in the method of the present invention are antibodies that bind to substantially the same epitope or epitopes as are recognized by monoclonal antibody LM609 and/or antibodies that bind to $\alpha_v/\beta_3$ competitively with LM609 (or an antigen binding fragment of LM609). Preferred antibodies useful in the present invention are those having affinity for such $\alpha_v/\beta_3$ epitope or epitopes which is greater than or equal to the affinity of LM609 for $\alpha_v/\beta_3$. A preferred $\alpha_v/\beta_3$ ligand compound useful in the present method is anti-$\alpha_v/\beta_3$ monoclonal antibody LM609. Monoclonal antibody LM609 (produced by hybridoma LM609 ATCC HB 9537) is disclosed in PCT Application Publication No. WO 89/05155 (published Jun. 15, 1989) and Cheresh et al., J. Biol. Chem., 1987, 262:17703–17711, the disclosures of which are incorporated herein by reference.

Other monoclonal antibodies useful in the present invention include antibodies capable of binding to substantially the same $\alpha_v/\beta_3$ epitope recognized by a monoclonal antibody selected from the group consisting of 10C4.1.3, 9G2.1.3, or 9D4.9.1, as described in PCT Application Publication Number WO 93/20229, the disclosure of which is incorporated herein by reference.

The term "monoclonal antibody" as used herein refers to a substantially homogeneous population of antibodies, that is, the individual antibodies comprising the population are identical in specificity and affinity except for possible naturally occurring mutations that may be present in minor amounts. The monoclonal antibodies of the invention can be used alone or as mixtures containing more than one monoclonal antibody population. The term monoclonal antibody as used herein includes hybrid, chimeric, or recombinant antibodies, such as "humanized" antibodies, regardless of species of origin or immunoglobulin class or subclass designation, as well as antibody fragments (including but not limited to, Fab, F(ab')$_2$ or Fv antibody fragments), so long as they contain the necessary antigen binding domain so as to have the desired binding properties as described herein.

The term "monoclonal" indicates the character of the antibody as a substantially homogeneous population of antibodies, and is not to be construed as requiring production of the antibody by any particular method. For example, the monoclonal antibodies of the invention may be made using the hybridoma method first described by Kohler and Milstein (Nature, 1975, 256:595) or may be made by recombinant DNA methods, using methods known in the art, for example but without limitation, using methods described in: PCT Publication Number WO 93/20229; Cabilly et al., U.S. Pat. No. 4,816,567; Koprowski, U.S. Pat. No. 4,172,124; Mage and Lamoyi, in Monoclonal Antibody Production Techniques and Applications, pp. 79–97 (Marcel Dekker, Inc., New York, 1987); Goding, in Monoclonal Antibodies: Principles an Practice, pp. 59–103 (Academic Press, 1986); Brodeur et al., in Monoclonal Antibody Production Techniques and Applications, pp. 51–63 (Marcel Dekker, Inc., New York, 1987); PCT Publication Number WO 92/22653; Johnson and Chiswell, Current Opinion in Structural Biology, 3:564–571, 1993.

Monoclonal antibodies useful in the method of the present invention include those that bind to soluble or cell associated $\alpha_v/\beta_3$ and which have the property of blocking the binding of vitronectin to $\alpha_v/\beta_3$. Antibodies useful in the present invention may also have the property of inhibiting other biological activities of $\alpha_v/\beta_3$, for example, inhibiting the binding of $\alpha_v/\beta_3$ to other ligands, such as fibrinogen.

The specificity of a monoclonal antibody for $\alpha_v/\beta_3$ expressed in various cell types may be determined so as to identify antibodies having substantial specificity for $\alpha_v/\beta_3$ expressed on a certain cell type, such as, for example, $\alpha_v/\beta_3$ expressed on melanoma tumor cells or endothelial cells or osteoclasts. Similarly, the specificity of the monoclonal antibody for $\alpha_v/\beta_3$ relative to other integrins or other proteins may be determined. The specificity of the monoclonal antibody may be expressed in terms of relative binding affinity.

The $\alpha_v/\beta_3$ ligands useful in the method of the present invention inhibit thrombosis by a different mechanism than any known method or agent for the treatment of thrombosis and associated thromboembolic disorders. Hence, the combination of the method of treatment of the present invention with other known methods for the treatment of thromboembolic disorders, may thereby provide a particularly effective therapy for many different heterogenous thromboembolic disorders.

The present invention also includes methods of using such selective $\alpha_v/\beta_3$ inhibitors in combination with one or more additional therapeutic agent(s), said additional agent being selected from: anti-coagulant or coagulation inhibitory agents, such as heparin or warfarin; anti-platelet or platelet inhibitory agents, such as aspirin, piroxicam, ticlopidine, or IIb/IIIa receptor antagonists; thrombin inhibitors such as boropeptides, hirudin, or argatroban; or thrombolytic or fibrinolytic agents, such as plasminogen activators (such as tissue plasminogen activator), anistreplase, urokinase, or streptokinase; or combinations thereof. Such combination treatments may be employed to achieve synergistic effects or effects additive or complementary to those provided by the methods of the present invention, such as, for example, in such uses as described above, particularly in the treatment, including prevention, of thromboembolic disorders.

The $\alpha_v/\beta_3$ ligands of the present invention can be administered in combination with one or more of the foregoing additional therapeutic agents, thereby to reduce the doses of each drug required to achieve the desired therapeutic effect. Thus, the combination treatment of the present invention permits the use of lower doses of each component, with reduced adverse, toxic effects of each component. A lower dosage minimizes the potential of side effects of the compounds, thereby providing an increased margin of safety relative to the margin of safety for each component when used as a single agent. Such combination therapies may be employed to achieve synergistic or additive therapeutic effects for the treatment of thromboembolic disorders.

By "administered in combination" or "combination treatment" it is meant that the $\alpha_v/\beta_3$ ligands and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

By "therapeutically effective" it is meant that amount of the $\alpha_v/\beta_3$ ligand of the present invention that when administered alone or in combination with an additional therapeutic agent to a cell or mammal is effective to prevent or ameliorate the thromboembolic disease condition or the progression of the disease.

According to another embodiment of the invention, the effectiveness of the $\alpha_v/\beta_3$ ligand in preventing or treating disease may be improved by administering the $\alpha_v/\beta_3$ ligand serially or in combination with another agent that is effective for the same clinical objective, such as another $\alpha_v/\beta_3$ ligand, or one or more additional therapeutic agents known for the intended therapeutic indication, for example, agents for the prevention or treatment of conditions associated with thrombosis such as, restenosis, unstable angina, and myocardial infarction.

The term "anti-coagulant agents" (or coagulation inhibitory agents), as used herein, denotes agents that inhibit blood coagulation. Such agents include warfarin, heparin, or low molecular weight heparin. The warfarin employed herein, may be, for example, crystalline warfarin or amorphous sodium warfarin. The heparin employed herein may be, for example, the sodium salt thereof.

The term "anti-platelet agents" (or platelet inhibitory agents), as used herein, denotes agents that inhibit platelet function such as by inhibiting the aggregation, adhesion or granular secretion of platelets. Such agents include the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicyclic acid or ASA) and piroxicam are preferred compounds. Other suitable anti-platelet agents include ticlopidine, including pharmaceutically acceptable salts or prodrugs thereof. Ticlopidine is also a preferred compound since it is known to be gentle on the gastro-intestinal tract in use. Still other suitable platelet inhibitory agents include GPIIb/IIIa receptor antagonists, thromboxane-A2-receptor antagonists and thromboxane-A2-synthetase inhibitors, as well as pharmaceutically acceptable salts or prodrugs thereof.

The term "thrombin inhibitors" (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. Such inhibitors include boroarginine derivatives and boropeptides, hirudin and argatroban, including pharmaceutically acceptable salts and prodrugs thereof. Boroarginine derivatives and boropeptides include N-acetyl and peptide derivatives of boronic acid, such as C-terminal α-aminoboronic acid derivatives of lysine, ornithine, arginine, homoarginine and corresponding isothiouronium analogs thereof. The term hirudin, as used herein, includes suitable derivatives or analogs of hirudin, such as hirulog or disulfatohirudin. Boropeptide thrombin inhibitors include compounds described in Kettner et al., U.S. Pat. No. 5,187,157 and European Patent Application Publication Number 293 881 A2, the disclosures of which are hereby incorporated herein by reference. Other suitable boroarginine derivatives and boropeptide thrombin inhibitors include those disclosed in PCT Application Publication Number 92/07869 and European Patent Application Publication Number 471,651 A2, the disclosures of which are hereby incorporated herein by reference, in their entirety.

The term "thrombolytics" (or fibrinolytic) agents (or thrombolytics or fibrinolytics), as used herein, denotes agents that lyse blood clots (thrombi). Such agents include tissue plasminogen activator, anistreplase, urokinase or streptokinase, including pharmaceutically acceptable salts or prodrugs thereof. The term anistreplase, as used herein, refers to anisoylated plasminogen streptokinase activator complex, as described, for example, in European Patent Application No. 028,489, the disclosures of which are hereby incorporated herein by reference herein, in their entirety. The term urokinase, as used herein, is intended to denote both dual and single chain urokinase, the latter also being referred to herein as prourokinase.

Administration of the $\alpha_v/\beta_3$ ligands useful in the method of the invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

Thromboembolic disorders are known to have a diverse pathophysiological makeup. There is a need for new therapeutic approaches for the treatment of these disorders which takes into account the diverse pathophysiological makeup of such diseases, and which includes therapeutic components which ameliorate each of the various pathophysiological aspects of the thromboemboic disorder. A combination treatment comprising administering to a host in need of such treatment an anti-coagulant agent such as warfarin or heparin, or an antiplatelet agent such as aspirin, piroxicam or ticlopidine, or a thrombin inhibitor such as a boropeptide, hirudin or argatroban, or a thrombolytic agent such as tissue plasminogen activator, anistreplase, urokinase or streptokinase, or combinations thereof, in combination with a $\alpha_v/\beta_3$ ligand useful in the method of the present invention, can provide such an approach. In addition, by administering lower doses of each, which is feasible where an additive or synergistic effect is involved, the incidence of any side effects associated with each alone at higher doses may be significantly reduced. Also, where a convenient single combination dosage unit is offered, it is generally accepted that such increased convenience to the patient results in an increase in compliance. Also, a single combination dosage unit would reduce the likelihood of patient confusion often associated with concurrent dosing of medication not available in a single dosage unit form.

The present invention includes combination products, that is, pharmaceutical compositions comprising an $\alpha_v/\beta_3$ ligand compound as described herein in combination with one or more of the following additional therapeutic agents: anti-coagulant agents such as warfarin or heparin; anti-platelet agents such as aspirin, piroxicam or ticlopidine; thrombin inhibitors such as boropeptides, hirudin or argatroban; thrombolytic agents such as tissue plasminogen activator, anistreplase, urokinase or streptokinase; or combinations thereof.

Another embodiment of present invention comprises a method of identifying an agent for the treatment of thrombosis which comprises:
(i) measuring the ability of test agents to inhibit the binding of vitronectin, or the binding of a ligand that binds competitively with vitronectin, to $\alpha_v/\beta_3$;
(ii) measuring the ability of the test agents to inhibit the the binding of fibrinogen, or the binding of a ligand that binds competitively with fibrinogen, to GPIIb/IIIa;
(iii) identifying the test agents which are substantially more effective inhibitors of $\alpha_v/\beta_3$ than GPIIb/IIIa based on the relative ability of the test agent to inhibit $\alpha_v/\beta_3$ and GPIIb/IIIa as measured in step (i) and (ii).

The present invention includes a method of identifying a compound for the treatment of thrombosis which comprises:
(i) measuring an inhibition parameter, such as an $IC_{50}$ or Ki, for test compounds for the inhibition of the binding of vitronectin, or a ligand that binds competitively with vitronectin, to $\alpha_v/\beta_3$;
(ii) measuring the inhibition parameter for test compounds for the inhibition the binding of fibrinogen, or a ligand that binds competitively with fibrinogen, to GPIIb/IIIa;
(iii) identifying the test compounds which are greater than 50-fold more effective as an inhibitor of $\alpha_v/\beta_3$ than GPIIb/IIIa based on the ratio of inhibition parameters determined in step (i) and (ii).

In a preferred method of the above embodiment of the invention, of identifying a compound for the treatment of thrombosis, step (iii) comprises identifying test compounds having an $IC_{50}$ in step (i) of less than about 10 nM and an $IC_{50}$ in step (ii) of greater than about 300 nM. Preferably the $IC_{50}$ values are determined in in vitro binding assays using purified $\alpha_v/\beta_3$ and GPIIb/IIIa receptors and purified vitronectin and fibrinogen or other adhesion protein that binds competitively with vitronectin or fibrinogen which is used in the assay.

Another embodiment of present invention comprises a method of identifying an agent for the treatment of thrombosis which comprises:
(i) measuring the ability of test agents to inhibit the binding of vitronectin, or the binding of a ligand that binds competitively with vitronectin, to $\alpha_v/\beta_3$;
(ii) measuring the ability of the test agents to inhibit platelet aggregation;
(iii) identifying the test agents which are substantially more effective as inhibitors Of $\alpha_v/\beta_3$ than as inhibitors of platelet aggregation based on the relative ability of the test agent to inhibit $\alpha_v/\beta_3$ and platelet aggregation as measured in step (i) and (ii).

In a preferred method of the above embodiment of the invention, of identifying a compound for the treatment of thrombosis, step (iii) comprises identifying test compounds having an $IC_{50}$ in step (i) of less than about 10 nM and an $IC_{50}$ in step (ii) of greater than about 1 $\mu$M. Preferably the $IC_{50}$ values are determined in in vitro assays using purified $\alpha_v/\beta_3$ and vitronectin or other adhesion protein that binds competively with vitronectin which is used in the assay and ex vivo blood platelets, such as in the assays described below.

Compounds useful in the method of the present invention are cyclic RGD-containing compounds of Formula I (SEQ ID NO:1):

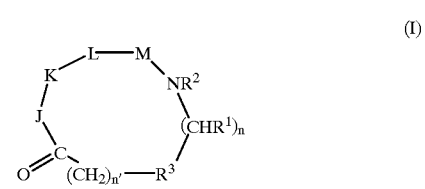

(I)

or a pharmaceutically acceptable salt form or prodrug form thereof wherein:
$R^1$ is H, $C_1$–$C_4$ alkyl, phenyl, benzyl or phenyl($C_1$–$C_4$)alkyl;
$R^2$ is H or methyl;
$R^3$ is

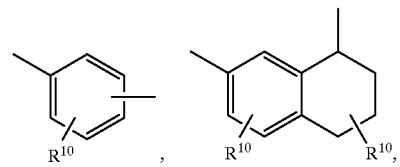

or -HET-;
HET is a 5 or 6-membered heterocycle selected from the group consisting of: furan, thiophene, pyrrole, imidazole, pyrazole, oxazole, isoxazole, oxazoline, isoxazoline, thiazole, isothizole, 1,2,4-triazole, 1,2,4-oxadiazole, 1,3,4-oxadiazole, 1.,2,4-thiadiazole, 1,3,4-thiadiazole, pyridine, pyridazine, pyrimidine, pyrazine, 1,2,3-triazine, 1,2,4-triazine, and 1,3,5-triazine and N-oxide forms thereof; said heterocycle being optionally substituted with $R^{10}$;
$R^{10}$ is H, halogen, $C_1$–$C_8$ alkyl, phenyl or $C_1$–$C_4$ alkoxy;
n is 0–2;
n' is 0–1;
J is Ala, Val, Ile, Leu, Nle, phenylGly, Phe, Lys, Orn, Met, Pro, β-Ala, Tyr, Ser, NMeGly, cyclohexylGly, cyclohexylmethylGly, norvaline, 2-aminobutyric acid, 2-aminopentanoic acid, Gly, Cys, S-benzyl-Cys, S-methyl-Cys, Asp, Glu, 2-amino-2-methylpropionic acid, His, 1-allo-isoleucine, Asn, Gln, Thr, Trp, or O-methyl-Tyr;

K is Arg, $N^\delta$-Me-$N^\delta$-guanidinylOrn, Lys, p-aminomethylPhe, p-guanidinylPhe, or $N^\epsilon$-MeLys;

L is Gly;

M is selected from Asp, β-MeAsp, NMeAsp, Asp-(methylcarbonyloxymethyl ester), Asp-(ethylcarbonyloxymethyl ester), Asp-(t-butylcarbonyloxymethyl ester), Asp-(cyclohexylcarbonyloxymethyl ester), Asp-(1-(methylcarbonyloxy)ethyl ester), Asp-(1-(ethylcarbonyloxy)ethyl ester), Asp-(1-(t-butylcarbonyloxy)ethyl ester), Asp-(1-(cyclohexylcarbonyloxy)ethyl ester), Asp-(i-propyloxycarbonyloxymethyl ester), Asp-(cyclohexylcarbonyloxymethyl ester), Asp-(t-butyloxycarbonyloxymethyl ester), Asp-(1-(i-propyloxycarbonyloxy)ethyl ester), Asp-(1-(cyclohexyloxycarbonyloxy)ethyl ester), Asp-(1-(t-butyloxycarbonyloxy)ethyl ester), Asp-(dimethylaminoethyl ester), Asp-(diethylaminoethyl ester), Asp-((1,3-dioxa-5-methyl-cyclopenten-2-one-4-yl)methyl ester), Asp-((5-(t-butyl)-1,3-dioxa-cyclopenten-2-one-4-yl)methyl ester), Asp-((1,3-dioxa-5-phenyl-cyclopenten-2-one-4-yl)methyl ester), or Asp-(1-(2-(2-methoxypropyl)carbonyloxy)ethyl ester).

Preferred compounds useful in the method of the present invention are compounds of Formula II (SEQ ID NO:1):

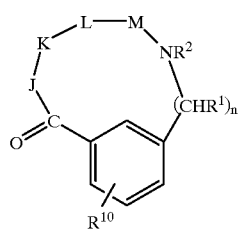

(II)

or a pharmaceutically acceptable salt or prodrug form thereof wherein:

$R^1$ is H, $C_1$–$C_4$ alkyl, phenyl, benzyl or phenyl($C_1$–$C_4$)alkyl;

$R^2$ is H or methyl;

$R^{10}$ is H, halogen, $C_1$–$C_8$ alkyl, phenyl or $C_1$–$C_4$ alkoxy;

alternatively, when $R^{10}$ is para to the carbonyl, $R^{10}$ and $R^1$ may be taken together to form —$CH_2$—$CH_2$—$CH_2$— thereby to form a six-membered fused ring;

n is 0–1;

J is Ala, Val, Ile, Leu, Nle, phenylGly, Phe, Lys, Orn, Met, Pro, β-Ala, Tyr, Ser, NMeGly, cyclohexylGly, cyclohexylmethylGly, norvaline, 2-aminobutyric acid, 2-aminopentanoic acid, Gly, Cys, S-benzyl-Cys, S-methyl-Cys, Asp, Glu, 2-amino-2-methylpropionic acid, His, 1-allo-isoleucine, Asn, Gln, Thr, Trp, or O-methyl-Tyr;

K is Arg, $N^\delta$-Me-$N^\delta$-guanidinylOrn, Lys or $N^\epsilon$-MeLys;

L is Gly; and

M is selected from Asp, P-MeAsp, NMeAsp, Asp-(methylcarbonyloxymethyl ester), Asp-(ethylcarbonyloxymethyl ester), Asp-(t-butylcarbonyloxymethyl ester), Asp-(cyclohexylcarbonyloxymethyl ester), Asp-(1-(methylcarbonyloxy)ethyl ester), Asp-(1-(ethylcarbonyloxy)ethyl ester), Asp-(1-(t-butylcarbonyloxy)ethyl ester), Asp-(1-(cyclohexylcarbonyloxy)ethyl ester), Asp-(i-propyloxycarbonyloxymethyl ester), Asp-(cyclohexylcarbonyloxymethyl ester), Asp-(t-butyloxycarbonyloxymethyl ester), Asp-(1-(i-propyloxycarbonyloxy)ethyl ester), Asp-(1-(cyclohexyloxycarbonyloxy)ethyl ester), Asp-(1-(t-butyloxycarbonyloxy)ethyl ester), Asp-(dimethylaminoethyl ester), Asp-(diethylaminoethyl ester), Asp-((1,3-dioxa-5-methyl-cyclopenten-2-one-4-yl)methyl ester), Asp-((5-(t-butyl)-1,3-dioxa-cyclopenten-2-one-4-yl)methyl ester), Asp-((1,3-dioxa-5-phenyl-cyclopenten-2-one-4-yl)methyl ester), or Asp-(1-(2-(2-methoxypropyl)carbonyloxy)ethyl ester).

Further preferred compounds useful in the present invention are those compounds of Formula (II) described above wherein:

n is 1;

K is Arg;

J is Ala, Val, Ile, Leu, Pro, Ser, or Lys.

Specifically preferred compounds useful in the method of the present invention are compounds of formula (IIa) (SEQ ID NO:1):

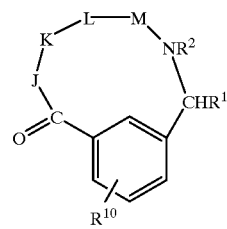

(IIa)

or a pharmaceutically acceptable prodrug or salt form thereof, selected from the group consisting of:

the compound of formula (IIa) wherein $R^1$, $R^2$ and $R^{10}$ are H; J is Ala; K is Arg; L is Gly; and M is Asp;

the compound of formula (IIa) wherein $R^1$, $R^2$ and $R^{10}$ are H; J is Val; K is Arg; L is Gly; and M is Asp;

the compound of formula (IIa) wherein $R^1$, $R^2$ and $R^{10}$ are H; J is Ile; K is Arg; L is Gly; and M is Asp;

the compound of formula (IIa) wherein $R^1$, $R^2$ and $R^{10}$ are H; J is Leu; K is Arg; L is Gly; and M is Asp;

the compound of formula (IIa) wherein $R^1$, $R^2$ and $R^{10}$ are H; J is Pro; K is Arg; L is Gly; and M is Asp;

the compound of formula (IIa) wherein $R^1$, $R^2$ and $R^{10}$ are H; J is Ser; K is Arg; L is Gly; and M is Asp;

the compound of formula (IIa) wherein $R^1$, $R^2$ and $R^{10}$ are H; J is Lys; K is Arg; L is Gly; and M is Asp.

Specifically preferred compounds useful in the method of the present invention are compounds, or pharmaceutically acceptable salt and prodrug forms thereof, selected from the group consisting of:

cyclo-(Ala-Arg-Gly-Asp-m-aminomethylbenzoic acid); (SEQ ID NO:2)

cyclo-(Pro-Arg-Gly-Asp-m-aminomethylbenzoic acid); (SEQ ID NO:3)

cyclo-(Ser-Arg-Gly-Asp-m-aminomethylbenzoic acid); (SEQ ID NO:4)

cyclo-(Leu-Arg-Gly-Asp-m-aminomethylbenzoic acid); (SEQ ID NO:5)

cyclo-(Lys-Arg-Gly-Asp-m-aminomethylbenzoic acid). (SEQ ID NO:6)

Another preferred embodiment of the present invention comprises a method of prevention or treatment of arterial or venous thrombosis in a host comprising administering to a host in need of such prevention or treatment a therapeutically effective amount of an agent, said agent being a substantially more effective inhibitor of $\alpha_v/\beta_3$ than GPIIb/IIIa based on the relative ability of the test agent to inhibit vitronectin binding to $\alpha_v/\beta_3$ and to inhibit fibrinogen to GPIIb/IIIa;

with the proviso that such agent is not a compound of Formula I: (SEQ ID NO:1)

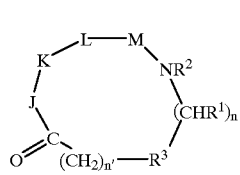

(I)

or a pharmaceutically acceptable salt form thereof wherein:
$R^1$ is H, $C_1$–$C_4$ alkyl, phenyl, benzyl or phenyl($C_1$–$C_4$)alkyl;
$R^2$ is H or methyl;
$R^3$ is

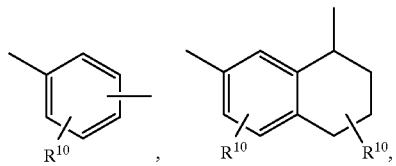

or -HET-;
HET is a 5 or 6-membered heterocycle selected from the group consisting of: furan, thiophene, pyrrole, imidazole, pyrazole, oxazole, isoxazole, oxazoline, isoxazoline, thiazole, isothizole, 1,2,4-triazole, 1,2,4-oxadiazole, 1,3,4-oxadiazole, 1.,2,4-thiadiazole, 1,3,4-thiadiazole, pyridine, pyridazine, pyrimidine, pyrazine, 1,2,3-triazine, 1,2,4-triazine, and 1,3,5-triazine and N-oxide forms thereof; said heterocycle being optionally substituted with $R^{10}$;
$R^{10}$ is H, halogen, $C_1$–$C_8$ alkyl, phenyl or $C_1$–$C_4$ alkoxy;
n is 0–2;
n' is 0–1;
J is Ala, Val, Ile, Leu, Nle, phenylGly, Phe, Lys, Orn, Met, Pro, β-Ala, Tyr, Ser, NMeGly, cyclohexylGly, cyclohexylmethylGly, norvaline, 2-aminobutyric acid, 2-aminopentanoic acid, Gly, Cys, S-benzyl-Cys, S-methyl-Cys, Asp, Glu, 2-amino-2-methylpropionic acid, His, 1-allo-isoleucine, Asn, Gln, Thr, Trp, or O-methyl-Tyr;
K is Arg, $N^\delta$-Me-$N^\delta$-guanidinylOrn, Lys, p-aminomethylPhe, p-guanidinylPhe, or $N^\epsilon$-MeLys;
L is Gly;
M is selected from Asp, β-MeAsp, NMeAsp, Asp-(methylcarbonyloxymethyl ester), Asp-(ethylcarbonyloxymethyl ester), Asp-(t-butylcarbonyloxymethyl ester), Asp-(cyclohexylcarbonyloxymethyl ester), Asp-(1-(methylcarbonyloxy)ethyl ester), Asp-(1-(ethylcarbonyloxy)ethyl ester), Asp-(1-(t-butylcarbonyloxy)ethyl ester), Asp-(1-(cyclohexylcarbonyloxy)ethyl ester), Asp-(i-propyloxycarbonyloxymethyl ester), Asp-(cyclohexylcarbonyloxymethyl ester), Asp-(t-butyloxycarbonyloxymethyl ester), Asp-(1-(i-propyloxycarbonyloxy)ethyl ester), Asp-(1-(cyclohexyloxycarbonyloxy)ethyl ester), Asp-(1-(t-butyloxycarbonyloxy)ethyl ester), Asp-(dimethylaminoethyl ester), Asp-(diethylaminoethyl ester), Asp-((1,3-dioxa-5-methyl-cyclopenten-2-one-4-yl)methyl ester), Asp-((5-(t-butyl)-1,3-dioxa-cyclopenten-2-one-4-yl) methyl ester), Asp-((1,3-dioxa-5-phenyl-cyclopenten-2-one-4-yl)methyl ester), or Asp-(1-(2-(2-methoxypropyl) carbonyloxy)ethyl ester).

Another embodiment of the present invention comprises a method of prevention or treatment of arterial or venous thrombosis in a host comprising administering to a host in need of such prevention or treatment a therapeutically effective amount of an agent, said agent being a substantially more effective inhibitor of $\alpha_v/\beta_3$ than GPIIb/IIIa based on the relative ability of the test agent to inhibit vitronectin binding to $\alpha_v/\beta_3$ and to inhibit fibrinogen to GPIIb/IIIa; with the proviso that such agent is not a linear or cyclic peptide comprising the sequence Arg-Gly-Asp.

Another preferred embodiment of the present invention comprises a method of prevention or treatment of arterial or venous thrombosis in a host comprising administering to a host in need of such prevention or treatment a therapeutically effective amount of an agent, said agent being a substantially more effective as an inhibitor of vitronectin binding to $\alpha_v/\beta_3$ than as an inhibitor of platelet aggregation;

with the proviso that such agent is not a compound of Formula I: (SEQ ID NO:1)

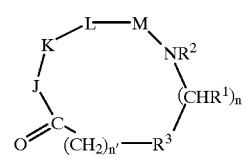

(I)

or a pharmaceutically acceptable salt form thereof wherein:
$R^1$ is H, $C_1$–$C_4$ alkyl, phenyl, benzyl or phenyl($C_1$–$C_4$)alkyl;
$R^2$ is H or methyl;
$R^3$ is

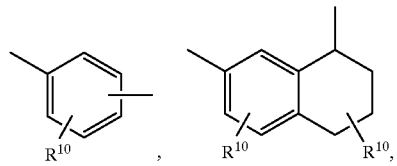

or -HET-;
HET is a 5 or 6-membered heterocycle selected from the group consisting of: furan, thiophene, pyrrole, imidazole, pyrazole, oxazole, isoxazole, oxazoline, isoxazoline, thiazole, isothizole, 1,2,4-triazole, 1,2,4-oxadiazole, 1,3,4-oxadiazole, 1.,2,4-thiadiazole, 1,3,4-thiadiazole, pyridine, pyridazine, pyrimidine, pyrazine, 1,2,3-triazine, 1,2,4-triazine, and 1,3,5-triazine and N-oxide forms thereof; said heterocycle being optionally substituted with $R^{10}$;
$R^{10}$ is H, halogen, $C_1$–$C_8$ alkyl, phenyl or $C_1$–$C_4$ alkoxy;
n is 0–2;
n' is 0–1;
J is Ala, Val, Ile, Leu, Nle, phenylGly, Phe, Lys, Orn, Met, Pro, β-Ala, Tyr, Ser, NMeGly, cyclohexylGly, cyclohexylmethylGly, norvaline, 2-aminobutyric acid, 2-aminopentanoic acid, Gly, Cys, S-benzyl-Cys, S-methyl-Cys, Asp, Glu, 2-amino-2-methylpropionic acid, His, 1-allo-isoleucine, Asn, Gln, Thr, Trp, or O-methyl-Tyr;

K is Arg, $N^\delta$-Me-$N^\delta$-guanidinylOrn, p-aminomethylPhe, p-guanidinylPhe, Lys or $N^\epsilon$-MeLys;

L is Gly;

M is selected from Asp, β-MeAsp, NMeAsp, Asp-(methylcarbonyloxymethyl ester), Asp-(ethylcarbonyloxymethyl ester), Asp-(t-butylcarbonyloxymethyl ester), Asp-(cyclohexylcarbonyloxymethyl ester), Asp-(1-(methylcarbonyloxy)ethyl ester), Asp-(1-(ethylcarbonyloxy)ethyl ester), Asp-(1-(t-butylcarbonyloxy)ethyl ester), Asp-(1-(cyclohexylcarbonyloxy)ethyl ester), Asp-(i-propyloxycarbonyloxymethyl ester), Asp-(cyclohexylcarbonyloxymethyl ester), Asp-(t-butyloxycarbonyloxymethyl ester), Asp-(1-(i-propyloxycarbonyloxy)ethyl ester), Asp-(1-(cyclohexyloxycarbonyloxy)ethyl ester), Asp-(1-(t-butyloxycarbonyloxy)ethyl ester), Asp-(dimethylaminoethyl ester), Asp-(diethylaminoethyl ester), Asp-((1,3-dioxa-5-methyl-cyclopenten-2-one-4-yl)methyl ester), Asp-((5-(t-butyl)-1,3-dioxa-cyclopenten-2-one-4-yl)methyl ester), Asp-((1,3-dioxa-5-phenyl-cyclopenten-2-one-4-yl)methyl ester), or Asp-(1-(2-(2-methoxypropyl)carbonyloxy)ethyl ester).

Another embodiment of the present invention comprises a method of prevention or treatment of arterial or venous thrombosis in a host comprising administering to a host in need of such prevention or treatment a therapeutically effective amount of an agent, said agent being a substantially more effective as an inhibitor of vitronectin binding to $\alpha_v/\beta_3$ than as an inhibitor of platelet aggregation; with the proviso that such agent is not a linear or cyclic peptide comprising the sequence Arg-Gly-Asp.

The assays described below may be used to demonstrate the preferred properties of the $\alpha_v/\beta_3$ vitronectin ligands useful in the method of the present invention.

The compounds herein described may have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. It will be appreciated that compounds of the present invention contain asymmetrically substituted carbon atoms, and may be isolated in optically active or racemic forms. It is well known in the art how to prepare optically active forms, such as by resolution of racemic forms or by synthesis, from optically active starting materials. Two distinct isomers (cis and trans) of the peptide bond are known to occur; both can also be present in the compounds described herein, and all such stable isomers are contemplated in the present invention. Unless otherwise specifically noted, the L-isomer of the amino acid is intended, for example, at positions J, K, L, and M of the compounds of Formula I and II. Except as provided in the preceding sentence, all chiral, diastereomeric, racemic forms and all geometric isomeric forms of a structure are intended, unless the specific stereochemistry or isomer form is specifically indicated. The D- and L-isomers of a particular amino acid are designated herein using the conventional 3-letter abbreviation of the amino acid, by way of example as D-Leu or Leu. As is conventionally understood, amino acids in a structural formula are oriented N-terminal to C-terminal and are joined by peptide bonds between amino acid residues. Thus, by way of example, in the compound of Formula II, the carboxy group of the aminoalkylbenzoic acid moiety is bonded to the alpha amino group of the J amino acid; and the amino group of the aminoalkylbenzoic acid moiety is bonded to the alpha carboxy group of the M amino acid When any variable (for example, $R^1$ or $R^{10}$) occurs more than one time in any constituent or in any formula, its definition on each occurrence is independent of its definition at every other occurrence. Thus, for example, if a group is shown to be substituted with 0–2 $R^{10}$, then said group may optionally be substituted with up to two $R^{10}$ and $R^{10}$ at each occurrence is selected independently from the defined list of possible $R^{10}$.

When a bond to a substituent is shown to cross the bond connecting two atoms in a ring, then such substituent may be bonded to any atom on the ring.

Combinations of substituents and/or variables are permissible only if such combinations result in stable compounds.

By "stable compound" it is meant herein a compound that is sufficiently robust to survive isolation to a useful degree of purity from a reaction mixture, and formulation into an efficacious therapeutic agent.

The term "substituted", as used herein, means that an one or more hydrogen on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

As used herein, "alkyl" is intended to include both branched and straight-chain saturated aliphatic hydrocarbon groups having the specified number of carbon atoms; "haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)); "alkoxy" represents an alkyl group of indicated number of carbon atoms attached through an oxygen bridge; "cycloalkyl" is intended to include saturated ring groups, including mono-,bi- or poly-cyclic ring systems, such as cyclopropyl, cyclobutyl, cyclopentyl, cyclohexyl, cycloheptyl, cyclooctyl and adamantyl; and "biycloalkyl" is intended to include saturated bicyclic ring groups such as [3.3.0]bicyclooctane, [4.3.0]bicyclononane, [4.4.0]bicyclodecane (decalin), [2.2.2]bicyclooctane, and so forth.

"Halo" or "halogen" as used herein refers to fluoro, chloro, bromo and iodo; and "counterion" is used to represent a small, negatively charged species such as chloride, bromide, hydroxide, acetate, sulfate and the like.

As used herein, "aryl" or "aromatic residue" is intended to mean phenyl or naphthyl. As used herein, "carbocycle" or "carbocyclic residue" is intended to mean any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" or "heterocyclic ring system" is intended to mean a stable 5- to 7-membered monocyclic or bicyclic or 7- to 10-membered bicyclic heterocyclic ring which may be saturated, partially unsaturated, or aromatic, and which consists of carbon atoms and from 1 to 4 heteroatoms selected independently from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, benzopyranyl, thiadiazine, tetrazolyl, benzofuranyl, benzothiophenyl, indolene, quinoline, isoquinolinyl or benzimidazolyl, piperidinyl, 4-piperidone, 2-pyrrolidone, tetrahydrofuran, tetrahydroquinoline, tetrahydroisoquinoline, decahydroquinoline, octahydroisoquinoline, azocine, triazine (including 1,2,3-, 1,2,4-, and 1,3,5-triazine), 6H-1,2,5-thiadiazine, 2H, 6H-1, 5,2-dithiazine, thiophene, tetrahydrothiophene, thianthrene, furan, pyran, isobenzofuran, chromene, xanthene, phenoxathiin, 2H-pyrrole, pyrrole, imidazole, pyrazole, thiazole, isothiazole, oxazole (including 1,2,4- and 1,3,4-oxazole), isoxazole, triazole, pyridine, pyrazine, pyrimidine, pyridazine, indolizine, isoindole, 3H-indole, indole, 1H-indazole, purine, 4H-quinolizine, isoquinoline, quinoline, phthalazine, naphthyridine, quinoxaline, quinazoline, cinnoline, pteridine, 4aH-carbazole, carbazole, β-carboline, phenanthridine, acridine, perimidine, phenanthroline, phenazine, phenarsazine, phenothiazine, furazan, phenoxazine, isochroman, chroman, pyrrolidine, pyrroline, imidazolidine, imidazoline, pyrazolidine, pyrazoline, piperazine, indoline, isoindoline, quinuclidine, or morpholine. Also included are fused ring and spiro compounds containing, for example, the above heterocycles.

"Prodrugs" are considered to be any covalently bonded carriers which release the active parent drug according to formula (I) in vivo when such prodrug is administered to a mammalian subject. Prodrugs of the compounds of formula (I) are prepared by modifying functional groups present in the compounds in such a way that the modifications are cleaved, either in routine manipulation or in vivo, to the parent compounds. Prodrugs include compounds of formula (I) wherein hydroxy, amine, or sulfhydryl groups are bonded to any group that, when administered to a mammalian subject, cleaves to form a free hydroxyl, amino, or sulfhydryl group, respectively. Examples of prodrugs include, but are not limited to, acetate, formate and benzoate derivatives of alcohol and amine functional groups in the compounds of formula (I); and the like.

As used herein, the term "any group that, when administered to a mammalian subject, cleaves to form a free hydroxyl, amino or sulfhydryl" means any group bonded to an O, N, or S atom, respectively, which is cleaved from the O, N, or S atom when the compound is administered to a mammalian subject to provide a compound having a remaining free hydroxyl, amino, or sulfhydryl group, respectively. Examples of groups that, when administered to a mammalian subject, are cleaved to form a free hydroxyl, amino or sulfhydryl, include but are not limited to, substituted $C_1$–$C_6$ alkyl, substituted $C_3$–$C_6$ alkoxyalkyl, substituted $C_1$–$C_6$ alkylcarbonyl, substituted $C_1$–$C_6$ alkoxycarbonyl, substituted $C_1$–$C_6$ alkylaminocarbonyl, substituted benzoyl, substituted phenoxycarbonyl, or substituted phenylaminocarbonyl groups. Examples of groups that, when administered to a mammalian subject, are cleaved to form a free hydroxyl, amino or sulfhydryl, may include certain hydroxy, amine or sulfhydryl protecting groups, respectively.

As used herein, "pharmaceutically acceptable salts" refer to derivatives of the disclosed compounds wherein the parent compound of formula (I) is modified by making acid or base salts of the compound of formula (I). Examples of pharmaceutically acceptable salts include, but are not limited to: mineral or organic acid salts of basic residues such as amines; alkali or organic salts of acidic residues such as carboxylic acids; and the like.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

The term "amino acid" as used herein means an organic compound containing both a basic amino group and an acidic carboxyl group. Included within this term are modified and unusual amino acids, such as those disclosed in, for example, Roberts and Vellaccio (1983) *The Peptides*, 5: 342–429, the teaching of which is hereby incorporated by reference. Modified or unusual amino acids which can be used to practice the invention include, but are not limited to, D-amino acids, hydroxylysine, 4-hydroxyproline, ornithine, 2,4-diaminobutyric acid, homoarginine, norleucine, N-methylaminobutyric acid, naphthylalanine, phenylglycine, β-phenylproline, tert-leucine, 4-aminocyclohexylalanine, N-methyl-norleucine, 3,4-dehydroproline, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid. Unusual amino acids can be synthesized by standard methods familiar to those skilled in the art. By way of example, the synthesis of unusual amino acids is described in *The Peptides: Analysis. Sythesis, Biology*, Vol. 5, pp. 342–449, Academic Press, New York (1981); N-alkyl amino acids can be prepared using procedures described previously (Cheung et al., (1977) Can. J. Chem. 55:906; Freidinger et al., (1982) J. Org. Chem. 48:77), which are incorporated herein by reference.

The term "amino acid residue" as used herein means that portion of an amino acid (as defined herein) that is present in a peptide.

The term "peptide" as used herein means a linear compound that consists of two or more amino acids (as defined herein) that are linked by means of a peptide bond. The term peptide also includes compounds containing both peptide and non-peptide components, such as pseudopeptide or peptide mimetic residues or other non-amino acid components. Such a compound containing both peptide and non-peptide components may also be referred to as a "peptide analog".

A "pseudopeptide" or "peptide mimetic" or peptidomimetic" is a compound which mimics the structure of an amino acid residue or a peptide, for example, by using linking groups other than amide linkages between the peptide mimetic and an amino acid residue (pseudopeptide bonds) and/or by using non-amino acid substituents and/or a modified amino acid residue.

A "pseudopeptide residue" means that portion of an pseudopeptide or peptide mimetic (as defined herein) that is present in a peptide.

The term "peptide bond" means a covalent amide linkage formed by loss of a molecule of water between the carboxyl group of one amino acid and the amino group of a second amino acid.

The term "pseudopeptide bonds" includes peptide bond isosteres which may be used in place of or as substitutes for the normal amide linkage. These substitute or amide "equivalent" linkages are formed from combinations of atoms not normally found in peptides or proteins which mimic the spatial requirements of the amide bond and which should stabilize the molecule to enzymatic degradation.

The following abbreviations are used herein:

| | |
|---|---|
| D-Abu | D-2-aminobutyric acid |
| β-Ala, b-Ala or βAla | 3-aminopropionic acid |
| Boc | t-butyloxycarbonyl |
| Boc-iodo-Mamb | t-butyloxycarbonyl-3-aminomethyl-4-iodobenzoic acid |
| Boc-Mamb | t-butyloxycarbonyl-3-aminomethylbenzoic acid |
| CBZ or Cbz | Carbobenzyloxy |
| di-NMeOrn | N-αMe-N-γMe-ornithine |
| NMeArg or MeArg | α-N-methyl arginine |
| NMeAmf | N-Methylaminomethylphenylalanine |
| NMeAsp | α-N-methyl aspartic acid |
| NMeGly or MeGly | N-methyl glycine |
| Mamb | 3-aminomethylbenzoic acid |
| OcHex | O-cyclohexyl |
| OBzl | O-benzyl |

The following conventional three-letter amino acid abbreviations are used herein; the conventional one-letter amino acid abbreviations are not used herein, except as specifically specified, for example in the case of RGD.

| | | |
|---|---|---|
| Ala | = | alanine |
| Arg | = | arginine |
| Asn | = | asparagine |
| Asp | = | aspartic acid |
| Cys | = | cysteine |
| Gln | = | glutamine |
| Glu | = | glutamic acid |
| Gly | = | glycine |
| His | = | histidine |
| Ile | = | isoleucine |
| Leu | = | leucine |
| Lys | = | lysine |
| Met | = | methionine |
| Nle | = | norleucine |
| Phe | = | phenylalanine |
| Phg | = | phenylglycine |
| Pro | = | proline |
| Ser | = | serine |
| Thr | = | threonine |
| Trp | = | tryptophan |
| Tyr | = | tyrosine |
| Val | = | valine |

The compounds of the present invention can be prepared in a number of ways well known to one skilled in the art of organic and peptide synthesis or using methods well known to one skilled in the art of molecular biology and protein expression and purification.

Peptide Synthesis

Compounds useful in the method of the present invention can be synthesized using standard synthetic methods known to those skilled in the art.

Generally, peptides are elongated by deprotecting the α-amine of the C-terminal residue and coupling the next suitably protected amino acid through a peptide linkage using the methods described. This deprotection and coupling procedure is repeated until the desired sequence is obtained. This coupling can be performed with the constituent amino acids in a stepwise fashion, or condensation of fragments (two to several amino acids), or combination of both processes, or by solid phase peptide synthesis according to the method originally described by Merrifield, J. Am. Chem. Soc., 85, 2149–2154 (1963), the disclosure of which is hereby incorporated by reference.

Compounds useful in the present invention may also be synthesized using automated peptide synthesizing equipment. In addition to the foregoing, procedures for peptide synthesis are described in: Stewart and Young, "Solid Phase Peptide Synthesis", 2nd ed, Pierce Chemical Co., Rockford, IL (1984); Gross, Meienhofer, Udenfriend, Eds., "The Peptides: Analysis, Synthesis, Biology", Vol. 1, 2, 3, 5, and 9, Academic Press, New York, (1980–1987); Bodanszky, "Peptide Chemistry: A Practical Textbook", Springer-Verlag, New York (1988); Bodanszky et al. "The Practice of Peptide Sythesis" Springer-Verlag, New York (1984); the disclosures of which are hereby incorporated by reference.

The coupling between two amino acid derivatives, an amino acid and a peptide, two peptide fragments, or the cyclization of a peptide can be carried out using standard coupling procedures such as the azide method, mixed carbonic acid anhydride (isobutyl chloroformate) method, carbodiimide (dicyclohexylcarbodiimide, diisopropylcarbodiimide, or water-soluble carbodiimides) method, active ester (p-nitrophenyl ester, N-hydroxysuccinic imido ester) method, Woodward reagent K method, carbonyldiimidazole method, phosphorus reagents such as BOP-Cl, or oxidation-reduction method. Some of these methods (especially the carbodiimide) can be enhanced by the addition of 1-hydroxybenzotriazole. These coupling reactions may be performed in either solution (liquid phase) or solid phase.

As is know in the art, the functional groups of the constituent amino acids must be protected during the coupling reactions to avoid undesired bonds being formed. The protecting groups that can be used are listed in Greene, "Protective Groups in Organic Synthesis" John Wiley & Sons, New York (1981) and "The Peptides: Analysis, Synthesis, Biology", Vol. 3, Academic Press, New York (1981), the disclosure of each of which is hereby incorporated by reference.

Compounds useful in the present invention may be prepared using methods described in PCT Publication Number WO93/07170 and WO94/22910 and WO94/11398, and in copending, commonly assigned U.S. patent application Ser. No. 07/949,285,abandoned, filed Sep. 9, 1992 and U.S. patent application Ser. No. 07/978,475,abandoned, filed Nov. 18, 1992. Monoclonal antibodies useful in the present invention may be prepared as disclosed in PCT Application Publication No. WO 89/05155 and PCT Application Publication Number WO 93/20229.

EXAMPLE 1

The specificity of compounds useful in the present invention for the $\alpha_v/\beta_3$ receptor relative to the GPIIb/IIIa receptor may be demonstrated in in vitro binding assays. Compounds may be tested for their ability to block binding of vitronectin to the $\alpha_v/\beta_3$ receptor and to block the binding of fibrinogen to GPIIb/IIIa receptor in the $\alpha_v/\beta_3$-Biotinylated Vitronectin Binding Assay and GPIIb/IIIa Receptor-Biotinylated Fibrinogen Binding Assay described below.

$\alpha_v/\beta_3$-Biotinylated Vitronectin Binding Assay

The $\alpha_v/\beta_3$ receptor was isolated from human placental extracts prepared using octylglucoside. The extract was passed over an anti-$\alpha_v/\beta_3$ monoclonal antibody (LM609) affinity column (prepared using LM609 and Affigel 10). The column was subsequently washed extensively at pH 7 and pH 4.5 followed by elution at pH 3. The resulting sample was concentrated by wheat germ agglutinin chromatography to provide a $\alpha_v/\beta_3$-containing sample which gave two bands on SDS-PAGE which were confirmed as $\alpha_v/\beta_3$ by western blotting.

The affinity purified $\alpha_v/\beta_3$ protein as described above was diluted at different levels and plated to 96 well plates (about 15 ng of $\alpha_v/\beta_3$ protein per well). ELISA detection of $\alpha_v/\beta_3$-bound biotinylated vitronectin was performed as described below using fixed concentration of biotinylated vitronectin (approximately 80 nM/well). This $\alpha_v/\beta_3$ receptor preparation contains the $\alpha_v/\beta_3$ with no detectable levels of $\alpha_v/\beta_5$ according to the gel and according to effects of blocking antibodies for the $\alpha_v/\beta_3$ or $\alpha_v/\beta_5$ in the ELISA.

A submaximal concentration of biotinylated vitronectin was selected based on concentration response curves with fixed $\alpha_v/\beta_3$ receptor concentration and variable concentrations of biotinylated vitronectin.

The purified $\alpha_v/\beta_3$ receptor is diluted with coating buffer (20 mM Tris HCl, 150 mM NaCl, 2.0 mM CaCl$_2$, 1.0 mM MgCl$_2$.6H$_2$O, 1.0 mM MnCl$_2$.4H$_2$O) and coated (100 $\mu$L/well) on Costar (3590) high capacity 96-well plates overnight at 4° C. The coating solution is discarded and the plates washed once with blocking/binding buffer (B/B buffer: 50 mM Tris HCl, 100 mM NaCl, 2.0 mM CaCl$_2$, 1.0 mM MgCl$_2$.6H$_2$O, 1.0 mM MnCl$_2$.4H$_2$O). The plate-immobilized $\alpha_v/\beta_3$ receptor is then blocked (200 $\mu$l/well) with 3.5% BSA in B/B buffer for 2 hours at room temperature. After washing once with 1.0% BSA in B/B buffer, biotinylated vitronectin (100 $\mu$L) and either test compound (inhibitor) (11 $\mu$L) or B/B buffer w/1.0% BSA (11 $\mu$L) is added to each well. The plates are incubated 2 hours at room temperature. The plates are washed twice with B/B buffer and incubated 1 hour at room temperature with anti-biotin alkaline phosphatase (100 $\mu$L/well) in B/B buffer containing 1.0% BSA. The plates are washed twice with B/B buffer and alkaline phosphatase substrate (100 $\mu$L) is added. Color is developed at room temperature. Color development is stopped by addition of 2N NaOH (25 $\mu$L/well) and absorbance is read at 405 nm.

The inhibitory binding constant ($K_i$) of test agents 30 may be calculated under this assay system using Michaelis-Menten analysis. The IC$_{50}$ is the concentration of test substance needed to block 50% of the vitronectin binding to the $\alpha_v/\beta_3$ receptor. The IC$_{50}$ for the inhibition of binding of vitronectin to the $\alpha_v/\beta_3$ receptor was determined based on time averaged values for the inhibition of vitronectin binding. Thus, the inhibition of vitronectin binding for each concentration of test compound was measured every 30 seconds over a 2 hour period and the average value of inhibition of vitronectin binding over such 2 hour period was used for the determination of the IC$_{50}$.

GPIIb/IIIa Receptor-Biotinylated Fibrinogen Binding Assay

The GPIIb/IIIa receptor was purified from human platelets according to D'Souza et al. (J. Biol. Chem., 1990, 265:3440–3446). The purified GPIIb/IIIa protein was coated on 96 well plates and the competition between test compound and biotinylated fibrinogen for binding to the plate-immobilized GPIIb/IIIa receptor was determined by ELISA as described below. Bound fibrinogen was detected using an avidin-alkaline phosphatase conjugate and paranitrophenol detection at 405 nM. For IC$_{50}$ determination, test agent was added at various concentrations to plates coated with purified GPIIb/IIIa protein which was followed by the addition of biotinylated fibrinogen. The inhibitory binding constant ($K_i$) of test agents were calculated under this assay system using standard Michaelis-Menten analysis. The IC$_{50}$ is the concentration of test substance needed to block 50% of the fibrinogen binding to the GPIIb/IIIa receptor.

The following reagents may be used in the GPIIb/IIIa-fibrinogen binding ELISA:

purified GPIIb/IIIa (148.8 $\mu$g/mL);

biotinylated fibrinogen (~1 mg/mL or 3000 nM);

anti-biotin alkaline phosphatase conjugate (Sigma no. A7418);

flat-bottom, high binding, 96-well plates (Costar Cat. no. 3590);

phosphatase substrate (Sigma 104) (40 mg capsules);

bovine serum albumin (BSA) (Sigma no. A3294);

Alkaline Phosphatase buffer—0.1 M glycine-HCl, 1 mM MgCl$_2$.6H$_2$O, 1 mM ZnCl$_2$, pH 10.4;

Binding buffer—20 mM Tris-HCl, 150 mM NaCl, 1 mM CaCl$_2$.2H$_2$O, 0.02% NaN$_3$, pH 7.0;

Buffer A—50 mM Tris-HCl, 100 mM NaCl, 2 mM CaCl$_2$.2H$_2$O, 0.02% NaN$_3$, pH 7.4;

Buffer A+3.5% BSA (Blocking buffer);

Buffer A+0.1% BSA (Dilution buffer);

2N NaOH.

The following method steps are used in the GPIIb/IIIa-fibrinogen binding ELISA:

Coat plates with GPIIb/IIIa in Binding buffer (125 ng/100 $\mu$L/well) overnight at 4° C. (Leave first column uncoated for non-specific binding). Cover and freeze plates at –70° C. until used. Thaw plate 1 hour at room temperature or overnight at 4° C. Discard coating solution and wash once with 200 $\mu$L Binding buffer per well. Block plate 2 hours at room temperature on shaker with 200 $\mu$l Buffer A+3.5% BSA (Blocking buffer) per well. Discard Blocking buffer and wash once with 200 $\mu$L Buffer A+0.1% BSA (Dilution buffer) per well. Pipet 11 $\mu$L of test compound (10× the concentration to be tested in Dilution buffer) into duplicate wells. Pipet 11 $\mu$l Dilution buffer into non-specific and total binding wells. Add 100 $\mu$L Biotinylated fibrinogen (1/133 in Dilution buffer, final concentration=20 nM) to each well. Incubate plates for 3 hours at room temperature on a plate shaker. Discard assay solution and wash twice with 300 $\mu$L Binding buffer per well. Add 100 $\mu$L anti-biotin alkaline phosphatase conjugate (1/1500 in Dilution buffer) to each well. Incubate plates for 1 hour at room temperature on plate shaker. Discard conjugate and wash twice with 300 $\mu$l Binding buffer per well. Add 100 $\mu$L phosphatase substrate (1.5 mg/ml in Alkaline phosphatase buffer) to each well. Incubate plate at room temperature on shaker until color develops. Stop color development by adding 25 $\mu$L 2N NaOH per well. Read plate at 405 nm. Blank against non-specific binding (NSB) well. % Inhibition is calculated as 100–(Test Compound Abs/Total Abs)×100.

Platelet Aggregation Assay

Venous blood was obtained from anesthetized mongrel dogs or from healthy human donors who were drug-free and aspirin-free for at least two weeks prior to blood collection. Blood was collected into citrated Vacutainer tubes. The blood was centrifuged for 15 minutes at 150× g (850 RPM in a Sorvall RT6000 Tabletop Centrifuge with H-1000 B rotor) at room temperature, and platelet-rich plasma (PRP) was removed. The remaining blood was centrifuged for 15 minutes at 1500× g (26,780 RPM) at room temperature, and platelet-poor plasma (PPP) was removed. Samples were assayed on an aggregometer (PAP-4 Platelet Aggregation Profiler), using PPP as the blank (100% transmittance). 200 μL of PRP (5×10$^8$ platelets/mL) were added to each micro test tube, and transmittance was set to 0%. 20 μl of ADP (10 μM) was added to each tube, and the aggregation profiles were plotted (% transmittance versus time). Test agent (20 μL) was added at different concentrations prior to the addition of the platelet agonist. Results are expressed as % inhibition of agonist-induced platelet aggregation.

The following representative compounds useful in the method of the present invention were tested in binding assays as described further below.

Compound A (SEQ ID NO:2). Compound A corresponds to Example 31 of PCT Publication Number WO93/07170 and WO94/22910 and copending, commonly assigned U.S. patent application Ser. No. 07/949,285, abandoned (cyclo-(Ala-Arg-Gly-Asp-Mamb).

Compound B (SEQ ID NO:3) is cyclo-(Pro-Arg-Gly-Asp-Mamb), which is described in PCT Publication Number WO93/07170 and WO94/22910 and copending, commonly assigned U.S. patent application Ser. No. 07/949,285, abandoned.

Compound C is anti-$\alpha_v/\beta_3$ monoclonal antibody LM609, which was obtained from Chemicon International Inc., Temecula, Calif.

Compound D (SEQ ID NO:6) is cyclo-(Lys-Arg-Gly-Asp-Mamb), which is described in PCT Publication Number WO93/07170 and WO94/22910 and copending, commonly assigned U.S. patent application Ser. NO. 07/949,285, abandoned.

Compound E (SEQ ID NO:5) is cyclo-(Leu-Arg-Gly-Asp-Mamb), which is Example 33a described in PCT Publication Number WO93/07170 and WO94/22910 and copending, commonly assigned U.S. patent application Ser. No. 07/949,285, abandoned.

The results of the receptor binding assays and platelet aggregation assay are summarized in Table 1.

TABLE 1

| Cpd | $\alpha_v/\beta_3$ IC$_{50}$ (nM) | GPIIb/IIIa IC$_{50}$ (nM) | Platelet Aggregation IC$_{50}$ (μM) | Relative Binding Affinity for $\alpha_v/\beta_3$ Relative to GPIIb/IIIa |
|---|---|---|---|---|
| A | 3.8 | 408 | 18 | 107 |
| B | 0.7 | 1520 | 44 | 2171 |
| C | <10 | >1000 | >10 | >100 |
| D | 1.9 | 359 | 23 | 189 |
| E | 1.4 | 430 | 41 | 307 |

As shown above, compounds A–E have IC$_{50}$ values for the inhibition of vitronectin binding to $\alpha_v/\beta_3$ of less than 5 nM and are relatively weak inhibitors of the binding of fibrinogen to GPIIb/IIIa with IC$_{50}$ values of greater than about 350 nM. Thus compounds A–E are substantially more effective as inhibitors of the binding of vitronectin to $\alpha_v/\beta_3$ than as inhibitors of the binding of fibrinogen to GPIIb/IIIa as measured in in vitro binding assays as described above. Compounds A–E are greater than about 100-fold more effective as inhibitors of the binding of vitronectin to $\alpha_v/\beta_3$ than as inhibitors of the binding of fibrinogen to GPIIb/IIIa, as measured by the ratio of the IC$_{50}$ values in the in vitro binding assays described above.

Also as shown above, compounds A–E have relatively weak in vitro platelet aggregation inhibitory activity, with IC$_{50}$ values of greater than about 10 μM. Thus, as shown in Table 1, compounds A–E are substantially more effective as inhibitors of the binding of vitronectin to $\alpha_v/\beta_3$ than as inhibitors of platelet aggregation, as measured in the in vitro binding and platelet aggregation assays described above. Compounds A–E are greater than about 1000-fold more effective as inhibitors of the binding of vitronectin to $\alpha_v/\beta_3$ than as inhibitors of platelet aggregation, as measured by the ratio of the IC$_{50}$ values in the in vitro binding and platelet aggregation assays described above.

EXAMPLE 2

The compounds useful in the present invention are effective in vivo in preventing thrombosis or rethrombosis without significantly effecting bleeding time or coagulation as shown in the in vivo tests described below.

Bleeding Time

The effect of compounds A–C on bleeding time (minutes) in anesthesized dogs was assessed on the backside of the tongue. A Simplate device (Organo Teknika) was applied to the surface of the tongue to make a uniform incision and blood was blotted with filter paper at 30 seconds intervals until bleeding completely stopped, with a 15 minutes cutoff time. Bleeding time was assessed before and at different intervals post-administration of test agent.

TABLE 2

In Vivo Platelet Aggregation Inhibition and Bleeding Time in Dog

| Test Compound, Dose | Platelet Aggregation Inhibition (%) | Bleeding Time (min) |
|---|---|---|
| saline | 0–20 | 3–5 |
| A | | |
| 1 mg/kg, IV | 0–10 | 3–4 |
| 3 mg/kg, IV | 10–20 | 3–4 |
| 10 mg/kg, IV | 30–50 | 5–6 |
| B | | |
| 1 mg/kg, IV | 0–10 | 3–4 |
| 3 mg/kg, IV | 0–10 | 3–4 |
| 10 mg/kg, IV | 10–20 | 3–4 |
| C | | |
| 0.1 mg/kg, IV | 0–10 | 3–4 |

Clotting Assay (Thrombin and Apothrombin Times)

Arterial blood samples were collected in 1/10th volume 3.8% sodium citrate and stored on ice for less than ten minutes. Samples were centrifuged (10,000× g, 1.5 minutes) and plasma separated from cellular components. Clotting assays were performed within 30 minutes of collection in a fibrometer (BBL Bibrosystem) at 37° C. Thrombin time determinations were performed at a final thrombin concentration of 4 units/mL. Activated partial thromboplastin time (also referred to as apothrombin time) (APTT) was determined by incubating 0.1 mL plasma with 0.1 mL APTT reagent (Sigma Chemical) for three minutes, followed by addition of 0.1 mL of 25 mM CaCl$_2$. Prothrombin time was determined by incubating 0.1 mL plasma with 0.1 mL thromboplastin, and clotting initiated by addition of 0.1 mL of 25 mM CaCl$_2$. Assays were performed in duplicate.

The effect of compound B on apothrombin time (APTT) and thrombin time (TT) in anesthesized dogs is shown in Table 3 below. As shown below compound B had no effect on apothrombin time or thrombin time.

TABLE 3

Effect of Compound B on Apothrombin Time and Thrombin Time in Dog

| Time Post Treatment (min) | Apothrombin Time (sec) | Thrombin Time (sec) |
|---|---|---|
| 0 (basal) | 12–14 | 7–9 |
| 30 | 13–14 | 8–9 |
| 60 | 12–14 | 8–9 |
| 90 | 12–14 | 7–8 |

Compound B was administered at 0.1 mg/kg, IV bolus followed by 0.4 mg/kg IV infusion for 2 hr.

EXAMPLE 3

The compounds useful in the method of the present invention are effective in preventing thrombus formation in vivo as demonstrated using the animal models of thrombosis described below. Compounds A, B and C were tested in an electrolytically induced femoral artery thrombosis and rethrombosis model in dogs as described below.

Carotid, Femoral Artery and Femoral Vein Thrombosis In Dogs (Electrolytic Injury Model)

The thrombosis model used in this study is a modification of the one described by Rote et al., J. Cardiovascular Pharmacolgy, 1993, 23:194–202. The experimental procedure provides the formation of a platelet rich intravascular thrombus at the site of the electrolytically-induced lesion in the arterial side. The femoral artery and carotid artery responses to the electrolytic injury are similar to that observed in the canine coronary artery in which intimal wall injury secondary to application of a direct anodal current leads to platelet adherence with the resultant occlusive thrombus formation (Rote et al., J. Cardiovascular Pharmacolgy, 1993, 23:194–202; Mousa et al., Circulation, 1994, 89:3–12). Animals were instrumented and a 20–30 mm segment of the femoral or carotid arteries were exposed and freed from facia, and branches were tied. Anodal current was applied using an intravascular electrode Penetration of the vessel wall by the electrode was facilitated by attaching the tip of a 23 gauge hypodermic needle to the uninsulated part of the electrode. Each intra-arterial electrode was connected to the positive pole (anodal) of a dual channel stimulator (Ni-Cad battery, 9 volts connected to 250,000 Ohm potentiometer in series). The cathode was connected to a distant subcutaneous site. The current delivered to the arterial wall was monitored continuously and maintained at 200 $\mu$A. Proper positioning of the electrode in the artery was confirmed by visual inspection at the end of each experiment. In all experiments the anodal current was applied for a maximum period of 3 hours. Arterial flow was monitored throughout the experiment by placing a doppler flow probe connected to a flow meter around the distal portion of the vessel segment. Similar procedures were applied to the femoral vein.

The effect of compounds A–C on the incidence of reocclusion, time to reocclusion, time to reperfusion and on thrombus weight after thrombolysis with streptokinase or tPA were measured. The results are shown in the Tables below.

TABLE 4

Effect of Compound A on Carotid Artery and Femoral Vein Thrombus Weight in Dog Thrombosis Model

| Compound | saline | compound A |
|---|---|---|
| Number | 4 | 3 |
| Dose |  | 1 mg/kg, IV bolus |
| Thrombus Weight (wet, mg) |  |  |
| right carotid artery | 51 ± 4 |  |
| left carotid artery |  | 14 ± 4* |
| right femoral vein | 18 ± 5 |  |
| left femoral vein |  | 4 ± 3* | current = 200 $\mu$A
Data represent mean ± SD
*P < 0.05

TABLE 5

Effect of Compound A on Carotid Artery and Femoral Vein Thrombus Weight in Dog Thrombosis Model

| Compound | saline | compound A |
|---|---|---|
| Number | 6 | 4 |
| Dose |  | 0.1 mg/kg, IV bolus + 0.4 mg/kg infusion for 3 hr |
| Thrombus Weight (wet, mg) |  |  |
| right carotid artery | 53 ± 4 |  |
| left carotid artery |  | 13 ± 2* |
| right femoral vein | 18 ± 5 |  |
| left femoral vein |  | 2 ± 1* | current = 200 $\mu$A
Data represent mean ± SD
*P < 0.05

TABLE 6

Effect of Compound C on Carotid Artery and Femoral Vein Thrombus Weight in Dog Thrombosis Model

| Compound | saline | compound C |
|---|---|---|
| Number | 44 | 3 |
| Dose |  | 0.07 mg/LCA injection (or 0.03 mg/LFV injection) bolus + 0.06 mg/kg infusion for 3 hr |
| Thrombus Weight (wet, mg) |  |  |
| right carotid artery | 65 ± 8 |  |
| left carotid artery |  | 16 ± 3* |
| right femoral vein | 25 ± 4 |  |
| left femoral vein |  | 7 ± 2* | current = 200 $\mu$A
Data represent mean ± SD
*P < 0.05

TABLE 7

Effect of Compound A and C on Carotid Artery Blood Flow and Occlusion in Canine Thrombosis Model

| Cpd | No. | Dose | Incidence of Occlusion | Blood Flow Basal (cm/sec) | Blood Flow End Occlusion | Time to Occlusion (min) |
|---|---|---|---|---|---|---|
| saline | 44 | 5 mL/kg, IV | 44/44 | 27.5 ±5.6 | 0 | 93 ±30.4 |
| A | 4* | 0.1 mg/kg, IV bolus + 0.4 mg/kg, IV infusion for 3 hr | 0/4 | 30.2 ±2.7 | 23.8 ±8.1 | >180 |
| A | 4* | 0.1 mg/kg, IV bolus + 0.1 mg/kg, IV infusion for 3 hr | 0/4 | 29.4 ±4.7 | 16.3 ±11 | >180 |
| C | 3 | 0.07 mg/IA + 0.06 mg/kg IV bolus + 0.06 mg/kg, IV infusion for 3 hr | 0/3 | 33.4 ±4.4 | 25 ± 7.0 | >180 |
| C | 1 | 0.07 mg/IA + 0.02 mg/kg, IV infusion for 3 hr | 1/1 | 22.5 ±10.2 | 0 | 62 ±18.8 |

*In 2 out 4 animals the experiment was terminated at the same time as the time for 100% occlusion in the control side.

TABLE 8

Effect of Compound A and C on Cyclic Flow Rate in Canine Thrombosis Model (Femoral Artery Oscillatory Flow)

| Cpd | No. | Dose | Cyclic Flow Rate (frequency/hr) |
|---|---|---|---|
| saline | 6 | 5 mL/kg, IV | 8 ± 5.5 |
| A | 4 | 0.1 mg/kg, IV bolus + 0.1 mg/kg, IV infusion for 3 hr | 0.5 ± 0.4* |
| C | 1 | 0.07 mg/IA + 0.02 mg/kg, IV infusion for 3 hr | 0.3* |
| C | 3 | 0.07 mg/IA + 0.06 mg/kg IV bolus + 0.06 mg/kg, IV infusion for 3 hr | 0 ± 0* |

*P < 0.01
Data represent mean ± SD.

TABLE 9

Effect of Compound C on Carotid Artery and Femoral Artery Blood Flow in Pig Thrombosis Model

| Compound | saline | Compound C |
|---|---|---|
| Dose | | 0.5 mg, IV bolus + 0.5 mg, IV infusion for 3 hr |
| Incidence of Occlusion | 3/3 | 0/3 |
| Time to Occlusion (min) | 50 ± 14 | >180 |
| Cyclic Flow Rate (frequency/hr) | 9 ± 3.5 | 0.5 ± 0.3 | average body weight of pigs = 19.5 ± 3.6 kg

EXAMPLE 4

Compounds useful in the method of the present invention are useful for the prevention of reocclusion as an adjunct to fibrinolytic therapy, as shown in the animal model tests described below. The effect of compound A in combination with tPA on the incidence of carotid artery reocclusion in dogs was assessed using a protocol as described by Mousa et al., Circulation 1994, 89:3–12. The results are summarized below.

TABLE 10

Effect of Compound A and tPA on Carotid Artery Reocclusion in Canine Thrombosis Model

| Compound | tPA | tPA + compound A |
|---|---|---|
| Number | 3 | 2 |
| Dose | 0.5 mg, carotid artery locally 1.5 mg, IV bolus | 0.1 mg/kg, IV bolus + 0.4 mg/kg, IV infusion for 3 hr |
| Time to Occlusion (min) | 80 ± 25 | 86–95 |
| Time to Reperfusion (min) | 15 ± 10 | 15–25 |
| Time to Reocclusion (min) | 23 ± 10 | >180 |

Data represent mean ± SD.

TABLE 11

Effect of Compound A and tPA on Carotid Artery Blood Flow and Thrombus Weight in Dog

| Compound | tPA | tPA + compound A |
|---|---|---|
| Number | 3 | 2 |
| Dose | 0.5 mg, carotid artery locally 1.5 mg, IV bolus | 0.1 mg/kg, IV bolus + 0.4 mg/kg, IV infusion for 3 hr |
| Thrombus Weight (wet, mg) | 36.2 ± 19.4 | 7.7–11 |
| Blood Flow (cm/sec) | | |
| Basal | 30 ± 2.5 | 25–31 |
| Reperfusion | 24.2 ± 8 | 17.5–37 |
| End | 0 | 12.5–17.5 |

Data represent mean ± SD.

Dosage and Formulation

The compounds useful in the method of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed as an anti-thrombotic agent.

The compounds useful in the method of the present invention can be administered by any means that produces contact of the active agent with the agent's site of action, $\alpha_v/\beta_3$, in the body of a mammal. They can be administered by any conventional means available for use in conjunction with pharmaceuticals, either as individual therapeutic agents or in a combination of therapeutic agents, such as an antiplatelet agent such as aspirin, piroxicam, ticlopidine, or a GPIIb/IIIa antagonist, or an anti-coagulant such as warfarin or heparin, or a thrombin inhibitor such as a boropeptide, hirudin or argatroban, or a thrombolytic agent such as tissue plasminogen activator, anistreplase, urokinase or streptokinase, or combinations thereof. The compounds of the invention, or compounds of the invention in combination with other therapeutic agents, can be administered alone, but generally administered with a pharmaceutical carrier selected on the basis of the chosen route of administration and standard pharmaceutical practice.

The dosage regimen for the compounds useful in the method of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

The dosage of the novel cyclic compounds of this invention administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Advantageously, compounds of the present invention may be administered in a single daily dose, or the total daily dosage may be administered in divided doses of two, three, or four times daily.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (compositions suitable for administration) contain from about 1 milligram to about 100 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences,* Mack Publishing Company, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

In the case where the $\alpha_v/\beta_3$ ligand of the present invention is an $\alpha_v/\beta_3$-specific antibody, such $\alpha_v/\beta_3$-specific antibody may be administered to a host in a pharmaceutically acceptable dosage form. Such antibody may be administered intravenously as a bolus or by continuous infusion over a period of time, by intramuscular, subcutaneous, intra-articular, intrasynovial, intrathecal, topical, or inhalation routes. Such dosage forms encompass pharmaceutically acceptable carriers that are inherently nontoxic and non-therapeutic. Examples of such carriers include ion exchangers, alumina, aluminum stearate, lecithin, serum proteins, such as human serum albumin, buffers such as phosphate or glycine, sorbic acid, potassium sorbate, partial glyceride mixtures of saturated vegetable fatty acids, water, salts, or electrolytes such as protamine sulfate, sodium chloride, metal salts, colloidal silica, magnesium trisilicate, polyvinyl pyrrolidone, cellulosic polymers, and polyethylene glycol. Carriers for topical or gel-based forms of antibody include polysaccharides such as sodium carboxymethylcellulose or methylcellulose, polyvinylpyrrolidone, polyacrylates, polyoxyethylene- polyoxypropylene-block polymers, polyethylene glycol, and wood wax alcohols. Conventional depot forms include, for example, microcapsules, nano-capsules, liposomes, plasters, sublingual tablets, and polymer matrices such as polylactide-:polyglycolide copolymers. When present in an aqueous dosage form, rather than being lyophilized, the antibody may be formulated, by way of examples and without limitation, at a concentration of about 0.1 mg/mL to 100 mg/mL, though wide variation outside of these ranges is permitted.

For the prevention or treatment of thrombosis, the appropriate dosage of such antibody will depend on the type of thromboembolic disorder to be treated, as defined above, the severity and course of the disease, whether the antibodies are administered for preventive or therapeutic purposes, the course of previous therapy, the patient's clinical history and response to the antibody, and the discretion of the attending physician. The antibody is suitably administered to the patient at one time or over a series of treatments.

Depending on the type and severity of the disease, by way of example and without limitation, about 0.015 to 15 mg of antibody/kg of patient weight is an initial candidate dosage for administration to the patient, whether, for example, by one or more separate administrations or by continuous infusion. For repeated administrations over several days or longer, depending on the condition, the treatment may be repeated until a desired suppression of disease symptoms occurs. However, other dosage regiments may be useful and are not excluded herefrom.

The compounds useful in the method of the present invention (the $\alpha_v/\beta_3$ ligand) may be administered in combination with a second therapeutic agent selected from: an anti-coagulant agent such as warfarin or heparin; an anti-platelet agent such as aspirin, piroxicam, ticlopidine, or a IIb/IIIa antagonist; a thrombin inhibitor such as a boropeptide thrombin inhibitor, or hirudin; or a thrombolytic agent such as plasminogen activators, such as tissue plasminogen activator, anistreplase, urokinase or streptokinase. The $\alpha_v/\beta_3$ ligand and such second therapeutic agent can be administered separately or as a physical combination in a single dosage unit, in any dosage form and by various routes of administration, as described above.

The $\alpha_v/\beta_3$ ligand of the present invention may be formulated together with the second therapeutic agent in a single dosage unit (that is, combined together in one capsule, tablet, powder, or liquid, etc.). When the $\alpha_v/\beta_3$ ligand and the second therapeutic agent are not formulated together in a single dosage unit, the $\alpha_v/\beta_3$ ligand and the second therapeutic agent (anti-coagulant agent, anti-platelet agent, thrombin inhibitor, and/or thrombolytic agent) may be administered essentially at the same time, or in any order; for example the $\alpha_v/\beta_3$ ligand may be administered first, followed by administration of the second agent (anti-coagulant agent, anti-platelet agent, thrombin inhibitor, and/or thrombolytic agent). When not administered at the same time, preferably the administration of the $\alpha_v/\beta_3$ ligand and the second therapeutic agent occurs less than about one hour apart.

A preferable route of administration of the $\alpha_v/\beta_3$ ligand is oral. Although it is preferable that the $\alpha_v/\beta_3$ ligand and the second therapeutic agent (anti-coagulant agent, anti-platelet agent, thrombin inhibitor, and/or thrombolytic agent) are both administered by the same route (that is, for example, both orally), if desired, they may each be administered by different routes and in different dosage forms (that is, for example, one component of the combination product may be administered orally, and another component may be administered intravenously).

The dosage of the $\alpha_v/\beta_3$ ligand when administered alone or in combination with a second therapeutic agent may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

Although the proper dosage of the the $\alpha_v/\beta_3$ ligand when administered in combination with the second therapeutic agent will be readily ascertainable by a medical practitioner skilled in the art, once armed with the present disclosure, by way of general guidance, where the compounds of this invention are combined with anti-coagulant agents, for example, a daily dosage may be about 0.1 to 100 milligrams of the $\alpha_v/\beta_3$ ligand and about 1 to 7.5 milligrams of the anticoagulant, per kilogram of patient body weight. For a tablet dosage form, the the $\alpha_v/\beta_3$ ligand may be present in an amount of about 1 to 10 milligrams per dosage unit, and the anti-coagulant in an amount of about 1 to 5 milligrams per dosage unit.

Where the $\alpha_v/\beta_3$ ligand is administered in combination with an anti-platelet agent, by way of general guidance, typically a daily dosage may be about 0.01 to 25 milligrams of the $\alpha_v/\beta_3$ ligand and about 50 to 150 milligrams of the additional anti-platelet agent, preferably about 0.1 to 1 milligrams of the $\alpha_v/\beta_3$ ligand and about 1 to 3 milligrams of antiplatelet agents, per kilogram of patient body weight.

Further, by way of general guidance, where the $\alpha_v/\beta_3$ ligand are adminstered in combination with thrombolytic agent, typically a daily dosage may be about 0.1 to 1 milligrams of the $\alpha_v/\beta_3$ ligand, per kilogram of patient body weight and, in the case of the thrombolytic agents, the usual dosage of the thrombolyic agent when administered alone may be reduced by about 70–80% when administered with a compound of Formula I.

Where two or more of the foregoing second therapeutic agents are administered with the $\alpha_v/\beta_3$ ligand, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the $\alpha_v/\beta_3$ ligand and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The present invention also includes pharmaceutical kits useful in the treatment of blood clots and/or the treatment of thromboembolic disorders, which comprise one or more containers containing a pharmaceutical composition comprising a therapeutically effective amount of the $\alpha_v/\beta_3$ ligand. Such kits may further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, may also be included in the kit.

The present invention also includes pharmaceutical kits useful in the treatment of blood clots and/or the treatment of thromboembolic disorders, which comprise one or more containers containing a pharmaceutical composition comprising a therapeutically effective amount of the $\alpha_v/\beta_3$ ligand and a therapeutically effective amount of a second therapeutic agent selected from one or more of the following: an anti-coagulant agent such as warfarin or heparin; an anti-platelet agent such as aspirin, piroxicam, ticlopidine, or a IIb/IIIa receptor antagonist; a thrombin inhibitor such as a boropeptide, hirudin or argatroban; or a thrombolytic agent such as tissue plasminogen activator, anistreplase, urokinase or streptokinase; or combinations thereof. Such therapeutic agents may be separate, or combined into a single dosage form as described above.

In the present disclosure it should be understood that the specified materials and conditions are important in practicing the invention but that unspecified materials and conditions are not excluded so long as they do not prevent the benefits of the invention from being realized.

What is claimed is:

1. A method of treating arterial or venous thrombosis in a mammalian host in need of such treatment comprising:

administering to the host a therapeutically effective amount of a monoclonal antibody having a laboratory designation selected from the group consisting of; LM609; 10C4.1.3; 9G2.1.3; and 9D4.9.1;

wherein the antibody inhibits the binding of vitronectin to $a_v/b_3$ with an $IC_{50}$ of less than 5 nM and inhibits the binding of fibrinogen to GPIIb/IIIa with an $IC_{50}$ of greater than 300 nM.

2. A method according to claim 1, wherein the monoclonal antibody is LM609.

3. A method according to claim 1, wherein the monoclonal antibody is 10C4.1.3.

4. A method according to claim 1, wherein the monoclonal antibody is 9G2.1.3.

5. A method according to claim 1, wherein the monoclonal antibody is 9D4.9.1.

6. A method according to claim 1, which further comprises administering to the host a therapeutically effective amount of one or more additional therapeutic agents selected from: a thrombolytic agent, an anti-coagulant agent, and an anti-platelet agent.

7. A method of treating arterial or venous thrombosis in a mammalian host in need of such treatment comprising:
   administering to the host a therapeutically effective amount of a monoclonal antibody having a laboratory designation selected from the group consisting of; LM609; 10C4.1.3; 9G2.1.3; and 9D1.9.1;
   wherein the antibody inhibits the binding of vitronectin to $a_v/b_3$ with an $IC_{50}$ of less than 10 nM and inhibits platelet aggregation with an $IC_{50}$ of greater than 1 $\mu$M.

8. A method according to claim 7, wherein the monoclonal antibody is LM609.

9. A method according to claim 7, wherein the monoclonal antibody is 10C4.1.3.

10. A method according to claim 7, wherein the monoclonal antibody is 9G2.1.3.

11. A method according to claim 7, wherein the monoclonal antibody is 9D4.9.1.

12. A method according to claim 7, which further comprises administering to the host a therapeutically effective amount of one or more additional therapeutic agents selected from; a thrombolytic agent, an anti-coagulant agent, and an anti-platelet agent.

* * * * *